US007124033B2

(12) United States Patent
Hinds et al.

(10) Patent No.: US 7,124,033 B2
(45) Date of Patent: Oct. 17, 2006

(54) METHOD FOR IDENTIFYING MATCHED GROUPS

(75) Inventors: David Hinds, Mountain View, CA (US); Renee Stokowski, San Jose, CA (US)

(73) Assignee: Perlegen Sciences, Inc., Mountain View, CA (US)

( * ) Notice: Subject to any disclaimer, the term of this patent is extended or adjusted under 35 U.S.C. 154(b) by 430 days.

(21) Appl. No.: 10/427,696

(22) Filed: Apr. 30, 2003

(65) Prior Publication Data

US 2004/0220750 A1 Nov. 4, 2004

(51) Int. Cl.
*G01N 33/48* (2006.01)
*G06G 7/48* (2006.01)
*C12Q 1/00* (2006.01)

(52) U.S. Cl. .............................. 702/19; 703/11; 435/4

(58) Field of Classification Search ..................... None
See application file for complete search history.

(56) References Cited

U.S. PATENT DOCUMENTS

| | | | | |
|---|---|---|---|---|
| 6,219,964 | B1 | 4/2001 | Byrum et al. | |
| 2002/0150909 | A1* | 10/2002 | Stuelpnagel et al. | 435/6 |
| 2003/0040870 | A1* | 2/2003 | Anderson et al. | 702/20 |
| 2003/0113758 | A1 | 6/2003 | Oudet et al. | |
| 2004/0022931 | A1 | 2/2004 | Staple et al. | |

OTHER PUBLICATIONS

Pritchard et al., "Inference of Population Structure Using Multilocus Genotype Data," Genetics Society of America, Genetics 155: 945-959 (Jun. 2000).

Ardlie et al., "Testing for Population Subdivision and Association in Four Case-Control Studies," Am. J. Hum. Genet. 71:304-311, (May 2002).

Pritchard et al., "Use of Unlinked Genetic Markers to Detect Population Stratification in Association Studies," Am. J. Hum. Genet. 65:220-228, (1999).

Rosenberg et al., "Genetic Structure of Human Populations," www.sciencemag.org, Science, vol. 298, 2381-2385, (Dec. 2002).

Bamshed et al., "Human Population Genetic Structure and Inference of Group Membership," Am. J. Hum. Genet. 72:578-589, (Dec. 2002)

J.C. Gower, Some Distance Properties of Latent Root and Vector Methods Used in Multivariate Analysis, Biometrika 1966 53, 3 and 4, p. 325-338.

Zhang et al., Quantitative Similarity-Based Association Test Using Population Samples, *Am. J. Hum. Genet.* 69:601-614, 2001.

McKeigue et al., Estimation of Admixture and Detection of Linkage in Admixed Populations by a Bayesian Approach: Application to African-American Populations, *Ann. Hum. Genet.* (2000), 64, 171-186.

Sham et al., "DNA Pooling: A Tool for Large-Scale Association Studies", www.nature.com/reviews/genetics, Nov. 2002, vol. 3, 862-871.

B. Devlin and K. Roeder, Genomic Control for Association Studies, Biometics 55, 997-1004, Dec. 1999.

Devlin et al., Unbiased Methods for Population-Based Association Studies, Genetic Epidemiology 21:273-284 (2001).

Reich et al., "Detecting Association in a Case-Control Study While Correcting for Population Stratification", Genetic Epidemiology 20:4-16 (2001).

Thompson et al., "Allelic Disequilibrium and Allele Frequency Distribution as a Function of Social and Demographic History," *Am J Hum Genet.* Jan. 1997;. 60(1):197-204

Notification from the International Searching Authority, International Application No. PCT/US04/13577, filing date Apr. 30, 2004, 2 pages.

* cited by examiner

*Primary Examiner*—John Brusca
*Assistant Examiner*—Russell Negin
(74) *Attorney, Agent, or Firm*—Beyer Weaver & Thomas, LLP

(57) ABSTRACT

Methods, code, and apparatus are used to ensure that groups of experimental subjects selected for inclusion in a study are matched. Individuals are genotyped and the genotype data is used to determine the extent of mismatch between study groups. If groups show evidence of poor matching, then the genotype data is used to better match the study groups.

28 Claims, 9 Drawing Sheets

| SNP | Case Group Allele X | Case Group Allele Y | Control Group Allele X | Control Group Allele Y | Chi Squared Statistic | p value |
|---|---|---|---|---|---|---|
| 1 | 140 | 60 | 131 | 69 | 0.73 | 0.39 |
| 2 | 115 | 85 | 91 | 109 | 5.29 | 0.02 |
| :<br>: | | | | | | |
| 312 | 86 | 114 | 80 | 120 | 0.25 | 0.61 |

Figure 6

| 600 | 602 | 604 | 608 | 610 |
|---|---|---|---|---|
| | $p < 0.1$ | $p < 0.01$ | $p < 0.001$ | $p<0.0001$ |
| Expected | 30 | 3 | 0 | 0 |
| Observed | 75 | 16 | 4 | 1 |

Figure 7A 700 702 704

| | Case Group | Control Group |
|---|---|---|
| 0.8-1 | 5 | 30 |
| 0.6-0.8 | 15 | 40 |
| 0.4-0.6 | 30 | 30 |
| 0.2-0.4 | 40 | 15 |
| 0-0.2 | 30 | 5 |

Figure 7B 700 702 704

| | Case Group | Control Group |
|---|---|---|
| 0.8-1 | 5 | 5 |
| 0.6-0.8 | 15 | 15 |
| 0.4-0.6 | 30 | 30 |
| 0.2-0.4 | 15 | 15 |
| 0-0.2 | 5 | 5 |

SEQUENCE LISTING

```
<160> NUMBER OF SEQ ID NOS: 313

<210> SEQ ID NO 1
<211> LENGTH: 9
<212> TYPE: DNA
<213> ORGANISM: Human

<400> SEQUENCE: 1
```

```
atgatgatg                                                                 9


<210> SEQ ID NO 2
<211> LENGTH: 25
<212> TYPE: DNA
<213> ORGANISM: Human

<400> SEQUENCE: 2

taccatcatt ttsgaattgt tcaga                                              25


<210> SEQ ID NO 3
<211> LENGTH: 25
<212> TYPE: DNA
<213> ORGANISM: Human

<400> SEQUENCE: 3

ggcctagagt tayggcattt cactt                                              25


<210> SEQ ID NO 4
<211> LENGTH: 25
<212> TYPE: DNA
<213> ORGANISM: Human

<400> SEQUENCE: 4

gagagttcaa tgygtaaaga tgccc                                              25


<210> SEQ ID NO 5
<211> LENGTH: 25
<212> TYPE: DNA
<213> ORGANISM: Human

<400> SEQUENCE: 5

taattggggt ttygtaacta gctac                                              25


<210> SEQ ID NO 6
<211> LENGTH: 25
<212> TYPE: DNA
<213> ORGANISM: Human

<400> SEQUENCE: 6

caattgctca tcragtccat gaaag                                              25


<210> SEQ ID NO 7
<211> LENGTH: 25
<212> TYPE: DNA
<213> ORGANISM: Human

<400> SEQUENCE: 7

ggtacgcttc aaygttatat gcggt                                              25


<210> SEQ ID NO 8
<211> LENGTH: 25
<212> TYPE: DNA
<213> ORGANISM: Human

<400> SEQUENCE: 8

gagatctcaa acyttaattt tactg                                              25


<210> SEQ ID NO 9
<211> LENGTH: 25
<212> TYPE: DNA
<213> ORGANISM: Human
```

<400> SEQUENCE: 9
caagctgaac ctsaatgtag ctcca 25

<210> SEQ ID NO 10
<211> LENGTH: 25
<212> TYPE: DNA
<213> ORGANISM: Human

<400> SEQUENCE: 10
gtgtcccact atwtaagaaa tgttt 25

<210> SEQ ID NO 11
<211> LENGTH: 25
<212> TYPE: DNA
<213> ORGANISM: Human

<400> SEQUENCE: 11
ttaaccgtct gtrctctcta cacgg 25

<210> SEQ ID NO 12
<211> LENGTH: 25
<212> TYPE: DNA
<213> ORGANISM: Human

<400> SEQUENCE: 12
tatatccaac cawctcttgg ctcta 25

<210> SEQ ID NO 13
<211> LENGTH: 25
<212> TYPE: DNA
<213> ORGANISM: Human

<400> SEQUENCE: 13
cgtaggccgt aamctgatgc catga 25

<210> SEQ ID NO 14
<211> LENGTH: 25
<212> TYPE: DNA
<213> ORGANISM: Human

<400> SEQUENCE: 14 cttactttc acsttactac ttgca 25

<210> SEQ ID NO 15
<211> LENGTH: 25
<212> TYPE: DNA
<213> ORGANISM: Human

<400> SEQUENCE: 15
tgagttatag agktgaatcc atgtg 25

<210> SEQ ID NO 16
<211> LENGTH: 25
<212> TYPE: DNA
<213> ORGANISM: Human

<400> SEQUENCE: 16
gaaaaccatt ctmaattcca gttcc 25

<210> SEQ ID NO 17
<211> LENGTH: 25
<212> TYPE: DNA
<213> ORGANISM: Human

-continued

<400> SEQUENCE: 17
ctaggagcta caratagttc caacc 25

<210> SEQ ID NO 18
<211> LENGTH: 25
<212> TYPE: DNA
<213> ORGANISM: Human

<400> SEQUENCE: 18
caatgggaga ttsaggccta gagca 25

<210> SEQ ID NO 19
<211> LENGTH: 25
<212> TYPE: DNA
<213> ORGANISM: Human

<400> SEQUENCE: 19
aaggtacata ttrggatgag atact 25

<210> SEQ ID NO 20
<211> LENGTH: 25
<212> TYPE: DNA
<213> ORGANISM: Human

<400> SEQUENCE: 20
ttgataattt gaytaaagct gacct 25

<210> SEQ ID NO 21
<211> LENGTH: 25
<212> TYPE: DNA
<213> ORGANISM: Human

<400> SEQUENCE: 21
actggctgcg cayggacaag tgtca 25

<210> SEQ ID NO 22
<211> LENGTH: 25
<212> TYPE: DNA
<213> ORGANISM: Human

<400> SEQUENCE: 22
tcattcttac caytggtgct gaaaa 25

<210> SEQ ID NO 23
<211> LENGTH: 25
<212> TYPE: DNA
<213> ORGANISM: Human

<400> SEQUENCE: 23
atttttcagc ttratttaac attgt 25

<210> SEQ ID NO 24
<211> LENGTH: 25
<212> TYPE: DNA
<213> ORGANISM: Human

<400> SEQUENCE: 24
taatctttat tgyattctca ttggc 25

<210> SEQ ID NO 25
<211> LENGTH: 25
<212> TYPE: DNA

-continued

<213> ORGANISM: Human

<400> SEQUENCE: 25
gacagtctgc aamaaaattt tctgg 25

<210> SEQ ID NO 26
<211> LENGTH: 25
<212> TYPE: DNA
<213> ORGANISM: Human

<400> SEQUENCE: 26
tttaccaggt ccrccaagac tatga 25

<210> SEQ ID NO 27
<211> LENGTH: 25
<212> TYPE: DNA
<213> ORGANISM: Human

<400> SEQUENCE: 27
tcacacaaag gcrtaatcat gaaaa 25

<210> SEQ ID NO 28
<211> LENGTH: 25
<212> TYPE: DNA
<213> ORGANISM: Human

<400> SEQUENCE: 28
ggaattgtgc taratacaaa aatgc 25

<210> SEQ ID NO 29
<211> LENGTH: 25
<212> TYPE: DNA
<213> ORGANISM: Human

<400> SEQUENCE: 29
acagaagtta agytaaacgt tctaa 25

<210> SEQ ID NO 30
<211> LENGTH: 25
<212> TYPE: DNA
<213> ORGANISM: Human

<400> SEQUENCE: 30
aataacttcc gcrtaatgag taccc 25

<210> SEQ ID NO 31
<211> LENGTH: 25
<212> TYPE: DNA
<213> ORGANISM: Human

<400> SEQUENCE: 31
ctggcttcag aastgatctt ttcct 25

<210> SEQ ID NO 32
<211> LENGTH: 25
<212> TYPE: DNA
<213> ORGANISM: Human

<400> SEQUENCE: 32
gtatttgtct gartcataga attta 25

<210> SEQ ID NO 33
<211> LENGTH: 25

<212> TYPE: DNA
<213> ORGANISM: Human

<400> SEQUENCE: 33
caagtcacat cargaagttg tggcc 25

<210> SEQ ID NO 34
<211> LENGTH: 25
<212> TYPE: DNA
<213> ORGANISM: Human

<400> SEQUENCE: 34
aacggaacaa tawtacattc ctggg 25

<210> SEQ ID NO 35
<211> LENGTH: 25
<212> TYPE: DNA
<213> ORGANISM: Human

<400> SEQUENCE: 35
ataagcagcc atmttattga gaagc 25

<210> SEQ ID NO 36
<211> LENGTH: 25
<212> TYPE: DNA
<213> ORGANISM: Human

<400> SEQUENCE: 36
taacaaacat aaratttgca ttata 25

<210> SEQ ID NO 37
<211> LENGTH: 25
<212> TYPE: DNA
<213> ORGANISM: Human

<400> SEQUENCE: 37
taaggagcta atrgccaata attac 25

<210> SEQ ID NO 38
<211> LENGTH: 25
<212> TYPE: DNA
<213> ORGANISM: Human

<400> SEQUENCE: 38
ggcagggaac cartctttag aaact 25

<210> SEQ ID NO 39
<211> LENGTH: 25
<212> TYPE: DNA
<213> ORGANISM: Human

<400> SEQUENCE: 39
ttcaaggaac ccrtgttgat aataa 25

<210> SEQ ID NO 40
<211> LENGTH: 25
<212> TYPE: DNA
<213> ORGANISM: Human

<400> SEQUENCE: 40
ttatactaca gaygttcatt atgcc 25

<210> SEQ ID NO 41

-continued

<211> LENGTH: 25
<212> TYPE: DNA
<213> ORGANISM: Human

<400> SEQUENCE: 41
gcagaatgcc ccrtccgtaa atgtc 25

<210> SEQ ID NO 42
<211> LENGTH: 25
<212> TYPE: DNA
<213> ORGANISM: Human

<400> SEQUENCE: 42
tttgaatcag agragtgatt ttgaa 25

<210> SEQ ID NO 43
<211> LENGTH: 25
<212> TYPE: DNA
<213> ORGANISM: Human

<400> SEQUENCE: 43
tctgcgatct ggmaatagag ctttc 25

<210> SEQ ID NO 44
<211> LENGTH: 25
<212> TYPE: DNA
<213> ORGANISM: Human

<400> SEQUENCE: 44
atacctctcc agycacacat aataa 25

<210> SEQ ID NO 45
<211> LENGTH: 25
<212> TYPE: DNA
<213> ORGANISM: Human

<400> SEQUENCE: 45
agtaatcact ttrtgtcaaa atgtt 25

<210> SEQ ID NO 46
<211> LENGTH: 25
<212> TYPE: DNA
<213> ORGANISM: Human

<400> SEQUENCE: 46
tcactagatg caratttctt catgt 25

<210> SEQ ID NO 47
<211> LENGTH: 25
<212> TYPE: DNA
<213> ORGANISM: Human

<400> SEQUENCE: 47
aatttcagca garggattat gatgc 25

<210> SEQ ID NO 48
<211> LENGTH: 25
<212> TYPE: DNA
<213> ORGANISM: Human

<400> SEQUENCE: 48
taaaattttc cargctggag caatt 25

-continued

<210> SEQ ID NO 49
<211> LENGTH: 25
<212> TYPE: DNA
<213> ORGANISM: Human

<400> SEQUENCE: 49
aacaatcgag gtwggcttta aagga 25

<210> SEQ ID NO 50
<211> LENGTH: 25
<212> TYPE: DNA
<213> ORGANISM: Human

<400> SEQUENCE: 50
gttagcacag ttyatagcaa gtctt 25

<210> SEQ ID NO 51
<211> LENGTH: 25
<212> TYPE: DNA
<213> ORGANISM: Human

<400> SEQUENCE: 51
attgcttggc acrttctcag aggtg 25

<210> SEQ ID NO 52
<211> LENGTH: 25
<212> TYPE: DNA
<213> ORGANISM: Human

<400> SEQUENCE: 52
cgcttcttgc agrggaactt catgg 25

<210> SEQ ID NO 53
<211> LENGTH: 25
<212> TYPE: DNA
<213> ORGANISM: Human

<400> SEQUENCE: 53
accatgttga garttgtgcc tagct 25

<210> SEQ ID NO 54
<211> LENGTH: 25
<212> TYPE: DNA
<213> ORGANISM: Human

<400> SEQUENCE: 54
gcagaccaga gastgtcaat ttaag 25

<210> SEQ ID NO 55
<211> LENGTH: 25
<212> TYPE: DNA
<213> ORGANISM: Human

<400> SEQUENCE: 55
acatcttaat gargtgctga cattt 25

<210> SEQ ID NO 56
<211> LENGTH: 25
<212> TYPE: DNA
<213> ORGANISM: Human

<400> SEQUENCE: 56
ctgatatagg ccrtagtgtc aggac 25

<210> SEQ ID NO 57
<211> LENGTH: 25
<212> TYPE: DNA
<213> ORGANISM: Human

<400> SEQUENCE: 57
catgagatgg ccrttttcca ggaga 25

<210> SEQ ID NO 58
<211> LENGTH: 25
<212> TYPE: DNA
<213> ORGANISM: Human

<400> SEQUENCE: 58
ataacatcct gcyggttact gatca 25

<210> SEQ ID NO 59
<211> LENGTH: 25
<212> TYPE: DNA
<213> ORGANISM: Human

<400> SEQUENCE: 59
ccctgggaac acrctactga gagcc 25

<210> SEQ ID NO 60
<211> LENGTH: 25
<212> TYPE: DNA
<213> ORGANISM: Human

<400> SEQUENCE: 60
tactatgggg aasaacttgt cactt 25

<210> SEQ ID NO 61
<211> LENGTH: 25
<212> TYPE: DNA
<213> ORGANISM: Human

<400> SEQUENCE: 61
aacttactgg aaygggaact tttca 25

<210> SEQ ID NO 62
<211> LENGTH: 25
<212> TYPE: DNA
<213> ORGANISM: Human

<400> SEQUENCE: 62
gataccctta tayggcagaa cttta 25

<210> SEQ ID NO 63
<211> LENGTH: 25
<212> TYPE: DNA
<213> ORGANISM: Human

<400> SEQUENCE: 63
ctgttgggaa acwcttcagt cacac 25

<210> SEQ ID NO 64
<211> LENGTH: 25
<212> TYPE: DNA
<213> ORGANISM: Human

<400> SEQUENCE: 64
gggtacaatt agrtcttact catgc 25

<210> SEQ ID NO 65
<211> LENGTH: 25
<212> TYPE: DNA
<213> ORGANISM: Human

<400> SEQUENCE: 65
caatttcgta cayttgaaag agaca 25

<210> SEQ ID NO 66
<211> LENGTH: 25
<212> TYPE: DNA
<213> ORGANISM: Human

<400> SEQUENCE: 66
gccttacaga gcygtgattt tggct 25

<210> SEQ ID NO 67
<211> LENGTH: 25
<212> TYPE: DNA
<213> ORGANISM: Human

<400> SEQUENCE: 67
aatcctgacg gtrggttcta caatt 25

<210> SEQ ID NO 68
<211> LENGTH: 25
<212> TYPE: DNA
<213> ORGANISM: Human

<400> SEQUENCE: 68
tttcaagagg tgygaggaca aggcc 25

<210> SEQ ID NO 69
<211> LENGTH: 25
<212> TYPE: DNA
<213> ORGANISM: Human

<400> SEQUENCE: 69
cattcctggc tgrtcgtaga caagg 25

<210> SEQ ID NO 70
<211> LENGTH: 25
<212> TYPE: DNA
<213> ORGANISM: Human

<400> SEQUENCE: 70
gaatcagaag gcraaatgtt tgggc 25

<210> SEQ ID NO 71
<211> LENGTH: 25
<212> TYPE: DNA
<213> ORGANISM: Human

<400> SEQUENCE: 71
aacgtggaac aasagtgaaa aaatg 25

<210> SEQ ID NO 72
<211> LENGTH: 25
<212> TYPE: DNA
<213> ORGANISM: Human

<400> SEQUENCE: 72

-continued gtgtttactc caraatacca gctta 25

<210> SEQ ID NO 73
<211> LENGTH: 25
<212> TYPE: DNA
<213> ORGANISM: Human

<400> SEQUENCE: 73
aaagggtcag tcrttgaaac attgc 25

<210> SEQ ID NO 74
<211> LENGTH: 25
<212> TYPE: DNA
<213> ORGANISM: Human

<400> SEQUENCE: 74
ccagtgcccg gcragtaacc aacgc 25

<210> SEQ ID NO 75
<211> LENGTH: 25
<212> TYPE: DNA
<213> ORGANISM: Human

<400> SEQUENCE: 75
aagtgtgcat aaygtagaga ctcat 25

<210> SEQ ID NO 76
<211> LENGTH: 25
<212> TYPE: DNA
<213> ORGANISM: Human

<400> SEQUENCE: 76
tgactttaga gcrtagtatt ttagc 25

<210> SEQ ID NO 77
<211> LENGTH: 25
<212> TYPE: DNA
<213> ORGANISM: Human

<400> SEQUENCE: 77
taggtggcaa atygataccc tgagg 25

<210> SEQ ID NO 78
<211> LENGTH: 25
<212> TYPE: DNA
<213> ORGANISM: Human

<400> SEQUENCE: 78
tgatttttgg atmggaaagg agact 25

<210> SEQ ID NO 79
<211> LENGTH: 25
<212> TYPE: DNA
<213> ORGANISM: Human

<400> SEQUENCE: 79
gcgaggacct atsggatgtg taggc 25

<210> SEQ ID NO 80
<211> LENGTH: 25
<212> TYPE: DNA
<213> ORGANISM: Human

<400> SEQUENCE: 80
catggcgctt tarcacaagt atgga 25

<210> SEQ ID NO 81
<211> LENGTH: 25
<212> TYPE: DNA
<213> ORGANISM: Human

<400> SEQUENCE: 81
tctgaaacca tcscaggaat gatgc 25

<210> SEQ ID NO 82
<211> LENGTH: 25
<212> TYPE: DNA
<213> ORGANISM: Human

<400> SEQUENCE: 82
ttctagtctc ctycccgggc ggtca 25

<210> SEQ ID NO 83
<211> LENGTH: 25
<212> TYPE: DNA
<213> ORGANISM: Human

<400> SEQUENCE: 83
gctgagaatt tcmagtgtga tcggt 25

<210> SEQ ID NO 84
<211> LENGTH: 25
<212> TYPE: DNA
<213> ORGANISM: Human

<400> SEQUENCE: 84
tggtttcttg caytgggagg gagac 25

<210> SEQ ID NO 85
<211> LENGTH: 25
<212> TYPE: DNA
<213> ORGANISM: Human

<400> SEQUENCE: 85
tatgtaaaag caygtgtcat tatga 25

<210> SEQ ID NO 86
<211> LENGTH: 25
<212> TYPE: DNA
<213> ORGANISM: Human

<400> SEQUENCE: 86
tcacattttc ttycaaaggc aagta 25

<210> SEQ ID NO 87
<211> LENGTH: 25
<212> TYPE: DNA
<213> ORGANISM: Human

<400> SEQUENCE: 87
ttactgaaca aaktatcatc tcagg 25

<210> SEQ ID NO 88
<211> LENGTH: 25
<212> TYPE: DNA
<213> ORGANISM: Human

<400> SEQUENCE: 88
tgaataatgc ctytagggtc tgaat 25

<210> SEQ ID NO 89
<211> LENGTH: 25
<212> TYPE: DNA
<213> ORGANISM: Human

<400> SEQUENCE: 89
cactttacgg ctytcaccat tcaca 25

<210> SEQ ID NO 90
<211> LENGTH: 25
<212> TYPE: DNA
<213> ORGANISM: Human

<400> SEQUENCE: 90
ctttgaaatc ttrtagttct gctgc 25

<210> SEQ ID NO 91
<211> LENGTH: 25
<212> TYPE: DNA
<213> ORGANISM: Human

<400> SEQUENCE: 91
ttcctcactg taytgcttat tctct 25

<210> SEQ ID NO 92
<211> LENGTH: 25
<212> TYPE: DNA
<213> ORGANISM: Human

<400> SEQUENCE: 92
gagcctggca taygaaacaa tttcc 25

<210> SEQ ID NO 93
<211> LENGTH: 25
<212> TYPE: DNA
<213> ORGANISM: Human

<400> SEQUENCE: 93
gaacacaata acraaacaga tgatg 25

<210> SEQ ID NO 94
<211> LENGTH: 25
<212> TYPE: DNA
<213> ORGANISM: Human

<400> SEQUENCE: 94
ctgggttgct tcytgtaaac ctgca 25

<210> SEQ ID NO 95
<211> LENGTH: 25
<212> TYPE: DNA
<213> ORGANISM: Human

<400> SEQUENCE: 95
ctaaaagtaa atrtcggtat cagtg 25

<210> SEQ ID NO 96
<211> LENGTH: 25
<212> TYPE: DNA
<213> ORGANISM: Human

-continued

<400> SEQUENCE: 96
tagatagcat gcrgcttcaa gaaga 25

<210> SEQ ID NO 97
<211> LENGTH: 25
<212> TYPE: DNA
<213> ORGANISM: Human

<400> SEQUENCE: 97
cagcgatgtt caytggcggc ttatt 25

<210> SEQ ID NO 98
<211> LENGTH: 25
<212> TYPE: DNA
<213> ORGANISM: Human

<400> SEQUENCE: 98
cactaatcaa gtrcactagc cctcc 25

<210> SEQ ID NO 99
<211> LENGTH: 25
<212> TYPE: DNA
<213> ORGANISM: Human

<400> SEQUENCE: 99
ctttttacca ctraactctg gaatg 25

<210> SEQ ID NO 100
<211> LENGTH: 25
<212> TYPE: DNA
<213> ORGANISM: Human

<400> SEQUENCE: 100
ttcaaatcat ccrcagactt gttca 25

<210> SEQ ID NO 101
<211> LENGTH: 25
<212> TYPE: DNA
<213> ORGANISM: Human

<400> SEQUENCE: 101
tgttttctgg acrcatagct catgt 25

<210> SEQ ID NO 102
<211> LENGTH: 25
<212> TYPE: DNA
<213> ORGANISM: Human

<400> SEQUENCE: 102
ctgggcaaat cawccattaa cactc 25

<210> SEQ ID NO 103
<211> LENGTH: 25
<212> TYPE: DNA
<213> ORGANISM: Human

<400> SEQUENCE: 103
ttttggagga ccwcaatcat ggttc 25

<210> SEQ ID NO 104
<211> LENGTH: 25
<212> TYPE: DNA

-continued

<213> ORGANISM: Human

<400> SEQUENCE: 104
attacctcct taygcaaatg accac 25

<210> SEQ ID NO 105
<211> LENGTH: 25
<212> TYPE: DNA
<213> ORGANISM: Human

<400> SEQUENCE: 105
gaatcgtggg gcrttttggc agcct 25

<210> SEQ ID NO 106
<211> LENGTH: 25
<212> TYPE: DNA
<213> ORGANISM: Human

<400> SEQUENCE: 106
acactacagt aayacctcta gccca 25

<210> SEQ ID NO 107
<211> LENGTH: 25
<212> TYPE: DNA
<213> ORGANISM: Human

<400> SEQUENCE: 107
aaacatgatt atkctcctgc attga 25

<210> SEQ ID NO 108
<211> LENGTH: 25
<212> TYPE: DNA
<213> ORGANISM: Human

<400> SEQUENCE: 108
ggaactggaa agmaacttcc atcag 25

<210> SEQ ID NO 109
<211> LENGTH: 25
<212> TYPE: DNA
<213> ORGANISM: Human

<400> SEQUENCE: 109
tgtcaggcac ttyagggcat tgacc 25

<210> SEQ ID NO 110
<211> LENGTH: 25
<212> TYPE: DNA
<213> ORGANISM: Human

<400> SEQUENCE: 110
ggagccatga garttattgc ggccc 25

<210> SEQ ID NO 111
<211> LENGTH: 25
<212> TYPE: DNA
<213> ORGANISM: Human

<400> SEQUENCE: 111
tgtgctttct gaygcctacc tccaa 25

<210> SEQ ID NO 112
<211> LENGTH: 25

<212> TYPE: DNA
<213> ORGANISM: Human

<400> SEQUENCE: 112
aagtggaggg cgytcattcc atcct 25

<210> SEQ ID NO 113
<211> LENGTH: 25
<212> TYPE: DNA
<213> ORGANISM: Human

<400> SEQUENCE: 113
gaaatcatgt ccrccctttt ccagt 25

<210> SEQ ID NO 114
<211> LENGTH: 25
<212> TYPE: DNA
<213> ORGANISM: Human

<400> SEQUENCE: 114
tacctattcg ccytccatga aacag 25

<210> SEQ ID NO 115
<211> LENGTH: 25
<212> TYPE: DNA
<213> ORGANISM: Human

<400> SEQUENCE: 115
tgagatttcc taygatggaa gtgtg 25

<210> SEQ ID NO 116
<211> LENGTH: 25
<212> TYPE: DNA
<213> ORGANISM: Human

<400> SEQUENCE: 116
ctgtttcctt tcyggttggt tcgtt 25

<210> SEQ ID NO 117
<211> LENGTH: 25
<212> TYPE: DNA
<213> ORGANISM: Human

<400> SEQUENCE: 117
cgcagtacaa ggyttcccta gtagt 25

<210> SEQ ID NO 118
<211> LENGTH: 25
<212> TYPE: DNA
<213> ORGANISM: Human

<400> SEQUENCE: 118
acagtatttg gayggctgac taaaa 25

<210> SEQ ID NO 119
<211> LENGTH: 25
<212> TYPE: DNA
<213> ORGANISM: Human

<400> SEQUENCE: 119
ctaaaagtgg acragagcct taaaa 25

<210> SEQ ID NO 120

<211> LENGTH: 25
<212> TYPE: DNA
<213> ORGANISM: Human

<400> SEQUENCE: 120
aaagcctcca cgsgacaaca gtttc 25

<210> SEQ ID NO 121
<211> LENGTH: 25
<212> TYPE: DNA
<213> ORGANISM: Human

<400> SEQUENCE: 121
gagacctcaa agrttcacaa catga 25

<210> SEQ ID NO 122
<211> LENGTH: 25
<212> TYPE: DNA
<213> ORGANISM: Human

<400> SEQUENCE: 122
tcactgcata taytaacata aaaac 25

<210> SEQ ID NO 123
<211> LENGTH: 25
<212> TYPE: DNA
<213> ORGANISM: Human

<400> SEQUENCE: 123
tattattatc ccrttgtaaa tgttt 25

<210> SEQ ID NO 124
<211> LENGTH: 25
<212> TYPE: DNA
<213> ORGANISM: Human

<400> SEQUENCE: 124
atattgtcac tgrtgccctt gattg 25

<210> SEQ ID NO 125
<211> LENGTH: 25
<212> TYPE: DNA
<213> ORGANISM: Human

<400> SEQUENCE: 125
gcacctaacc atytgctgac gtggc 25

<210> SEQ ID NO 126
<211> LENGTH: 25
<212> TYPE: DNA
<213> ORGANISM: Human

<400> SEQUENCE: 126
ttacaggttt caytttttta tcgtc 25

<210> SEQ ID NO 127
<211> LENGTH: 25
<212> TYPE: DNA
<213> ORGANISM: Human

<400> SEQUENCE: 127
aaaagtttag gawcatagta aggtt 25

-continued

<210> SEQ ID NO 128
<211> LENGTH: 25
<212> TYPE: DNA
<213> ORGANISM: Human

<400> SEQUENCE: 128
aaactctatg ctktggcctt tcata 25

<210> SEQ ID NO 129
<211> LENGTH: 25
<212> TYPE: DNA
<213> ORGANISM: Human

<400> SEQUENCE: 129
cattatgaat tcyttcgtca ctgat 25

<210> SEQ ID NO 130
<211> LENGTH: 25
<212> TYPE: DNA
<213> ORGANISM: Human

<400> SEQUENCE: 130
aaggcagagc ackttctgt ggttc 25

<210> SEQ ID NO 131
<211> LENGTH: 25
<212> TYPE: DNA
<213> ORGANISM: Human

<400> SEQUENCE: 131
tttagaaata gcyggtgatt acaga 25

<210> SEQ ID NO 132
<211> LENGTH: 25
<212> TYPE: DNA
<213> ORGANISM: Human

<400> SEQUENCE: 132
tacagaacct tasacagact acgta 25

<210> SEQ ID NO 133
<211> LENGTH: 25
<212> TYPE: DNA
<213> ORGANISM: Human

<400> SEQUENCE: 133
cagagcttat tcsttctacc ttgtt 25

<210> SEQ ID NO 134
<211> LENGTH: 25
<212> TYPE: DNA
<213> ORGANISM: Human

<400> SEQUENCE: 134
gcatgtctca carcattacg aatgg 25

<210> SEQ ID NO 135
<211> LENGTH: 25
<212> TYPE: DNA
<213> ORGANISM: Human

<400> SEQUENCE: 135
tgcatagtaa tcyttcattc agcac 25

<210> SEQ ID NO 136
<211> LENGTH: 25
<212> TYPE: DNA
<213> ORGANISM: Human

<400> SEQUENCE: 136
tagctacagt taycgattcc gctta 25

<210> SEQ ID NO 137
<211> LENGTH: 25
<212> TYPE: DNA
<213> ORGANISM: Human

<400> SEQUENCE: 137
agtatttgtc aaytaatgct gttaa 25

<210> SEQ ID NO 138
<211> LENGTH: 25
<212> TYPE: DNA
<213> ORGANISM: Human

<400> SEQUENCE: 138
aaggctttcc tgkaaaagta gctgt 25

<210> SEQ ID NO 139
<211> LENGTH: 25
<212> TYPE: DNA
<213> ORGANISM: Human

<400> SEQUENCE: 139
tagcagcatt camgggactc aggtg 25

<210> SEQ ID NO 140
<211> LENGTH: 25
<212> TYPE: DNA
<213> ORGANISM: Human

<400> SEQUENCE: 140
gcaatagcta atygagttcc tgatt 25

<210> SEQ ID NO 141
<211> LENGTH: 25
<212> TYPE: DNA
<213> ORGANISM: Human

<400> SEQUENCE: 141
tactttgatt aawggctgat gatat 25

<210> SEQ ID NO 142
<211> LENGTH: 25
<212> TYPE: DNA
<213> ORGANISM: Human

<400> SEQUENCE: 142
ttaaaatttg tcsgtgccaa tttag 25

<210> SEQ ID NO 143
<211> LENGTH: 25
<212> TYPE: DNA
<213> ORGANISM: Human

<400> SEQUENCE: 143
tacctgtgta aakaaattga taaca 25

<210> SEQ ID NO 144
<211> LENGTH: 25
<212> TYPE: DNA
<213> ORGANISM: Human

<400> SEQUENCE: 144
gtccaattag cartaagtgc catgc 25

<210> SEQ ID NO 145
<211> LENGTH: 25
<212> TYPE: DNA
<213> ORGANISM: Human

<400> SEQUENCE: 145
cttttgttca ttkgataatc gggtg 25

<210> SEQ ID NO 146
<211> LENGTH: 25
<212> TYPE: DNA
<213> ORGANISM: Human

<400> SEQUENCE: 146
gaatgtctgc tcrgttacaa cgtga 25

<210> SEQ ID NO 147
<211> LENGTH: 25
<212> TYPE: DNA
<213> ORGANISM: Human

<400> SEQUENCE: 147
gcatgtattg tcyatccaaa aactt 25

<210> SEQ ID NO 148
<211> LENGTH: 25
<212> TYPE: DNA
<213> ORGANISM: Human

<400> SEQUENCE: 148
aattcagacc acrcttaggg aatca 25

<210> SEQ ID NO 149
<211> LENGTH: 25
<212> TYPE: DNA
<213> ORGANISM: Human

<400> SEQUENCE: 149
gtccacaaag gtytggaata taaaa 25

<210> SEQ ID NO 150
<211> LENGTH: 25
<212> TYPE: DNA
<213> ORGANISM: Human

<400> SEQUENCE: 150
ttgtgatatt cckccaaagt aaaca 25

<210> SEQ ID NO 151
<211> LENGTH: 25
<212> TYPE: DNA
<213> ORGANISM: Human

<400> SEQUENCE: 151

-continued tctgtacctc atktacttgt agtct 25

<210> SEQ ID NO 152
<211> LENGTH: 25
<212> TYPE: DNA
<213> ORGANISM: Human

<400> SEQUENCE: 152
actcaggtgc atycagagcc gaagg 25

<210> SEQ ID NO 153
<211> LENGTH: 25
<212> TYPE: DNA
<213> ORGANISM: Human

<400> SEQUENCE: 153
agtcaatgct tayttaagct tattc 25

<210> SEQ ID NO 154
<211> LENGTH: 25
<212> TYPE: DNA
<213> ORGANISM: Human

<400> SEQUENCE: 154
acatggtagc agraaatgag agcgt 25

<210> SEQ ID NO 155
<211> LENGTH: 25
<212> TYPE: DNA
<213> ORGANISM: Human

<400> SEQUENCE: 155
gttataaagc ctytccaggt gcaga 25

<210> SEQ ID NO 156
<211> LENGTH: 25
<212> TYPE: DNA
<213> ORGANISM: Human

<400> SEQUENCE: 156
tcaagtgcct gcyacaagta aatag 25

<210> SEQ ID NO 157
<211> LENGTH: 25
<212> TYPE: DNA
<213> ORGANISM: Human

<400> SEQUENCE: 157
catgtataag ccraaagcta aaacg 25

<210> SEQ ID NO 158
<211> LENGTH: 25
<212> TYPE: DNA
<213> ORGANISM: Human

<400> SEQUENCE: 158
cactcgagca tgyggcatta tttaa 25

<210> SEQ ID NO 159
<211> LENGTH: 25
<212> TYPE: DNA
<213> ORGANISM: Human

<400> SEQUENCE: 159

-continued atcagtcatt tcyggctctt tatgt 25

<210> SEQ ID NO 160
<211> LENGTH: 25
<212> TYPE: DNA
<213> ORGANISM: Human

<400> SEQUENCE: 160
agccaaacca tayctagttt ccaaa 25

<210> SEQ ID NO 161
<211> LENGTH: 25
<212> TYPE: DNA
<213> ORGANISM: Human

<400> SEQUENCE: 161
atgtgatact taygaattcc accag 25

<210> SEQ ID NO 162
<211> LENGTH: 25
<212> TYPE: DNA
<213> ORGANISM: Human

<400> SEQUENCE: 162
gtacctctag acrtccatac agctt 25

<210> SEQ ID NO 163
<211> LENGTH: 25
<212> TYPE: DNA
<213> ORGANISM: Human

<400> SEQUENCE: 163
acagctgagt garaacaaaa tggac 25

<210> SEQ ID NO 164
<211> LENGTH: 25
<212> TYPE: DNA
<213> ORGANISM: Human

<400> SEQUENCE: 164
tacagtacag acrttgatga gacca 25

<210> SEQ ID NO 165
<211> LENGTH: 25
<212> TYPE: DNA
<213> ORGANISM: Human

<400> SEQUENCE: 165
agtcttatct ttsggacaaa tggaa 25

<210> SEQ ID NO 166
<211> LENGTH: 25
<212> TYPE: DNA
<213> ORGANISM: Human

<400> SEQUENCE: 166
tccaagcctc ccrgaatgaa acttt 25

<210> SEQ ID NO 167
<211> LENGTH: 25
<212> TYPE: DNA
<213> ORGANISM: Human

<400> SEQUENCE: 167
ccacttctaa tasctttcac aagac 25

<210> SEQ ID NO 168
<211> LENGTH: 25
<212> TYPE: DNA
<213> ORGANISM: Human

<400> SEQUENCE: 168
cgtaaactga gcwgacctgt accct 25

<210> SEQ ID NO 169
<211> LENGTH: 25
<212> TYPE: DNA
<213> ORGANISM: Human

<400> SEQUENCE: 169
ctgtgttaaa ctyccagatg gcagt 25

<210> SEQ ID NO 170
<211> LENGTH: 25
<212> TYPE: DNA
<213> ORGANISM: Human

<400> SEQUENCE: 170
cagctggaaa casgtctggg ctctt 25

<210> SEQ ID NO 171
<211> LENGTH: 25
<212> TYPE: DNA
<213> ORGANISM: Human

<400> SEQUENCE: 171
gttaaccagc ctraatgcaa aaagt 25

<210> SEQ ID NO 172
<211> LENGTH: 25
<212> TYPE: DNA
<213> ORGANISM: Human

<400> SEQUENCE: 172
aacagccaga gtycctgtaa gagca 25

<210> SEQ ID NO 173
<211> LENGTH: 25
<212> TYPE: DNA
<213> ORGANISM: Human

<400> SEQUENCE: 173
ggcatacatc ttycttaacc tacat 25

<210> SEQ ID NO 174
<211> LENGTH: 25
<212> TYPE: DNA
<213> ORGANISM: Human

<400> SEQUENCE: 174
ggtccaaaag tcstgctagg tatct 25

<210> SEQ ID NO 175
<211> LENGTH: 25
<212> TYPE: DNA
<213> ORGANISM: Human

<400> SEQUENCE: 175
ggcaagacct caraataact taaag 25

<210> SEQ ID NO 176
<211> LENGTH: 25
<212> TYPE: DNA
<213> ORGANISM: Human

<400> SEQUENCE: 176
atgcgtaggt tawggtccta gttca 25

<210> SEQ ID NO 177
<211> LENGTH: 25
<212> TYPE: DNA
<213> ORGANISM: Human

<400> SEQUENCE: 177
gtgctacttt gamtgtgaaa ataca 25

<210> SEQ ID NO 178
<211> LENGTH: 25
<212> TYPE: DNA
<213> ORGANISM: Human

<400> SEQUENCE: 178
ctcaggaaag aaytgccact tcgaa 25

<210> SEQ ID NO 179
<211> LENGTH: 25
<212> TYPE: DNA
<213> ORGANISM: Human

<400> SEQUENCE: 179
atttgatgtg acygatagct ccaga 25

<210> SEQ ID NO 180
<211> LENGTH: 25
<212> TYPE: DNA
<213> ORGANISM: Human

<400> SEQUENCE: 180
cagagccaaa aaygttgctc ttcca 25

<210> SEQ ID NO 181
<211> LENGTH: 25
<212> TYPE: DNA
<213> ORGANISM: Human

<400> SEQUENCE: 181
atgctactga taygtaatca caatg 25

<210> SEQ ID NO 182
<211> LENGTH: 25
<212> TYPE: DNA
<213> ORGANISM: Human

<400> SEQUENCE: 182
accctttcta ctrtactatc acagc 25

<210> SEQ ID NO 183
<211> LENGTH: 25
<212> TYPE: DNA

-continued

<213> ORGANISM: Human

<400> SEQUENCE: 183
cagtgttctt tgrggttcca ctctt 25

<210> SEQ ID NO 184
<211> LENGTH: 25
<212> TYPE: DNA
<213> ORGANISM: Human

<400> SEQUENCE: 184
ctagtgcttt caygatgccc ttagt 25

<210> SEQ ID NO 185
<211> LENGTH: 25
<212> TYPE: DNA
<213> ORGANISM: Human

<400> SEQUENCE: 185
gttaccctta caygtggctg tttgc 25

<210> SEQ ID NO 186
<211> LENGTH: 25
<212> TYPE: DNA
<213> ORGANISM: Human

<400> SEQUENCE: 186
ttctaactct cawttaagtg aggca 25

<210> SEQ ID NO 187
<211> LENGTH: 25
<212> TYPE: DNA
<213> ORGANISM: Human

<400> SEQUENCE: 187
ctcacattac ccractttgg gccct 25

<210> SEQ ID NO 188
<211> LENGTH: 25
<212> TYPE: DNA
<213> ORGANISM: Human

<400> SEQUENCE: 188
gccaatgttt agyggagata tttct 25

<210> SEQ ID NO 189
<211> LENGTH: 25
<212> TYPE: DNA
<213> ORGANISM: Human

<400> SEQUENCE: 189
tgttcaagcc atygatatta ggttg 25

<210> SEQ ID NO 190
<211> LENGTH: 25
<212> TYPE: DNA
<213> ORGANISM: Human

<400> SEQUENCE: 190
gtgtgatgct ctyttttgac ccaca 25

<210> SEQ ID NO 191
<211> LENGTH: 25

<212> TYPE: DNA
<213> ORGANISM: Human

<400> SEQUENCE: 191
cttttctaat acygcaatat ttcaa 25

<210> SEQ ID NO 192
<211> LENGTH: 25
<212> TYPE: DNA
<213> ORGANISM: Human

<400> SEQUENCE: 192
tgaaacttag gcrgaatagt aagta 25

<210> SEQ ID NO 193
<211> LENGTH: 25
<212> TYPE: DNA
<213> ORGANISM: Human

<400> SEQUENCE: 193
tatcatggga ccrtcctata aggtt 25

<210> SEQ ID NO 194
<211> LENGTH: 25
<212> TYPE: DNA
<213> ORGANISM: Human

<400> SEQUENCE: 194
tggagagagg ccrtttccta atcag 25

<210> SEQ ID NO 195
<211> LENGTH: 25
<212> TYPE: DNA
<213> ORGANISM: Human

<400> SEQUENCE: 195
cctgaatgta atsaatatgt gacag 25

<210> SEQ ID NO 196
<211> LENGTH: 25
<212> TYPE: DNA
<213> ORGANISM: Human

<400> SEQUENCE: 196
gcattggcct gayggatagg ctgct 25

<210> SEQ ID NO 197
<211> LENGTH: 25
<212> TYPE: DNA
<213> ORGANISM: Human

<400> SEQUENCE: 197
gtaatctagc camaacaatg gttgc 25

<210> SEQ ID NO 198
<211> LENGTH: 25
<212> TYPE: DNA
<213> ORGANISM: Human

<400> SEQUENCE: 198
gtttgtaaat ttygtggatt gaaag 25

<210> SEQ ID NO 199

-continued

<211> LENGTH: 25
<212> TYPE: DNA
<213> ORGANISM: Human

<400> SEQUENCE: 199
taaaggaaaa tamttgaagt gttgg 25

<210> SEQ ID NO 200
<211> LENGTH: 25
<212> TYPE: DNA
<213> ORGANISM: Human

<400> SEQUENCE: 200
cccaggaatt tcraaaggga gcaca 25

<210> SEQ ID NO 201
<211> LENGTH: 25
<212> TYPE: DNA
<213> ORGANISM: Human

<400> SEQUENCE: 201
ggagtagaga aasacaacct caata 25

<210> SEQ ID NO 202
<211> LENGTH: 25
<212> TYPE: DNA
<213> ORGANISM: Human

<400> SEQUENCE: 202
taaaaggcag targaaggca gtcca 25

<210> SEQ ID NO 203
<211> LENGTH: 25
<212> TYPE: DNA
<213> ORGANISM: Human

<400> SEQUENCE: 203
ttctgctgga aamttagggt gatca 25

<210> SEQ ID NO 204
<211> LENGTH: 25
<212> TYPE: DNA
<213> ORGANISM: Human

<400> SEQUENCE: 204
tttcccctgt caktttagca atcaa 25

<210> SEQ ID NO 205
<211> LENGTH: 25
<212> TYPE: DNA
<213> ORGANISM: Human

<400> SEQUENCE: 205
tcctatatgg tgycccaaat tctta 25

<210> SEQ ID NO 206
<211> LENGTH: 25
<212> TYPE: DNA
<213> ORGANISM: Human

<400> SEQUENCE: 206
gcctcctttc aamcctggtg agaag 25

-continued

<210> SEQ ID NO 207
<211> LENGTH: 25
<212> TYPE: DNA
<213> ORGANISM: Human

<400> SEQUENCE: 207
gaaatgttcc cargtccagc catga 25

<210> SEQ ID NO 208
<211> LENGTH: 25
<212> TYPE: DNA
<213> ORGANISM: Human

<400> SEQUENCE: 208
ttttagcgag ggwtcattcg ttcat 25

<210> SEQ ID NO 209
<211> LENGTH: 25
<212> TYPE: DNA
<213> ORGANISM: Human

<400> SEQUENCE: 209
atcataaaaa atygccactc gagaa 25

<210> SEQ ID NO 210
<211> LENGTH: 25
<212> TYPE: DNA
<213> ORGANISM: Human

<400> SEQUENCE: 210
tgaaaccaac cawgggtctc tcatc 25

<210> SEQ ID NO 211
<211> LENGTH: 25
<212> TYPE: DNA
<213> ORGANISM: Human

<400> SEQUENCE: 211
attttggtaa acrggaccag cattt 25

<210> SEQ ID NO 212
<211> LENGTH: 25
<212> TYPE: DNA
<213> ORGANISM: Human

<400> SEQUENCE: 212
tccaattcat gakgaaagcc taagt 25

<210> SEQ ID NO 213
<211> LENGTH: 25
<212> TYPE: DNA
<213> ORGANISM: Human

<400> SEQUENCE: 213
gagcttttcc caygtatgat ctgac 25

<210> SEQ ID NO 214
<211> LENGTH: 25
<212> TYPE: DNA
<213> ORGANISM: Human

<400> SEQUENCE: 214
ctagatctct tascagttta atcct 25

<210> SEQ ID NO 215
<211> LENGTH: 25
<212> TYPE: DNA
<213> ORGANISM: Human

<400> SEQUENCE: 215
caaactttga ctyttggtac taaga 25

<210> SEQ ID NO 216
<211> LENGTH: 25
<212> TYPE: DNA
<213> ORGANISM: Human

<400> SEQUENCE: 216
catcattgga caycatgaaa tatgt 25

<210> SEQ ID NO 217
<211> LENGTH: 25
<212> TYPE: DNA
<213> ORGANISM: Human

<400> SEQUENCE: 217
atgaggaaaa ttyggtacat tcatt 25

<210> SEQ ID NO 218
<211> LENGTH: 25
<212> TYPE: DNA
<213> ORGANISM: Human

<400> SEQUENCE: 218
aagtcattca casacacaag tgatt 25

<210> SEQ ID NO 219
<211> LENGTH: 25
<212> TYPE: DNA
<213> ORGANISM: Human

<400> SEQUENCE: 219
tgactaaaaa gaytgagcgt ttgtg 25

<210> SEQ ID NO 220
<211> LENGTH: 25
<212> TYPE: DNA
<213> ORGANISM: Human

<400> SEQUENCE: 220
acctaatatc taygaagcca attgt 25

<210> SEQ ID NO 221
<211> LENGTH: 25
<212> TYPE: DNA
<213> ORGANISM: Human

<400> SEQUENCE: 221
tcagggatca tarcactgac aaaag 25

<210> SEQ ID NO 222
<211> LENGTH: 25
<212> TYPE: DNA
<213> ORGANISM: Human

<400> SEQUENCE: 222
actaagatgc tgrgaagact gcagg 25

<210> SEQ ID NO 223
<211> LENGTH: 25
<212> TYPE: DNA
<213> ORGANISM: Human

<400> SEQUENCE: 223
ttgcacggga gcrgttacaa cattt 25

<210> SEQ ID NO 224
<211> LENGTH: 25
<212> TYPE: DNA
<213> ORGANISM: Human

<400> SEQUENCE: 224
gcatatcaga aaygtatgac cacaa 25

<210> SEQ ID NO 225
<211> LENGTH: 25
<212> TYPE: DNA
<213> ORGANISM: Human

<400> SEQUENCE: 225
tgaaaccaag ttygtactct tggct 25

<210> SEQ ID NO 226
<211> LENGTH: 25
<212> TYPE: DNA
<213> ORGANISM: Human

<400> SEQUENCE: 226
atttaatttg taytctttcg gaaat 25

<210> SEQ ID NO 227
<211> LENGTH: 25
<212> TYPE: DNA
<213> ORGANISM: Human

<400> SEQUENCE: 227
aaatactgct taygtaactt aagag 25

<210> SEQ ID NO 228
<211> LENGTH: 25
<212> TYPE: DNA
<213> ORGANISM: Human

<400> SEQUENCE: 228
aaagtctctt tcrtattagc taaac 25

<210> SEQ ID NO 229
<211> LENGTH: 25
<212> TYPE: DNA
<213> ORGANISM: Human

<400> SEQUENCE: 229
ggcctaaaac carccacttt atatg 25

<210> SEQ ID NO 230
<211> LENGTH: 25
<212> TYPE: DNA
<213> ORGANISM: Human

<400> SEQUENCE: 230
tggcttccaa gartcccctg gtcag 25

<210> SEQ ID NO 231
<211> LENGTH: 25
<212> TYPE: DNA
<213> ORGANISM: Human

<400> SEQUENCE: 231
ttttcattga tasaagggtg agcca 25

<210> SEQ ID NO 232
<211> LENGTH: 25
<212> TYPE: DNA
<213> ORGANISM: Human

<400> SEQUENCE: 232
aaagcagcaa gtytggccat ctaga 25

<210> SEQ ID NO 233
<211> LENGTH: 25
<212> TYPE: DNA
<213> ORGANISM: Human

<400> SEQUENCE: 233
attctgcagg gaycatggcc agttt 25

<210> SEQ ID NO 234
<211> LENGTH: 25
<212> TYPE: DNA
<213> ORGANISM: Human

<400> SEQUENCE: 234
agataaacct ttyaccacgt ctaga 25

<210> SEQ ID NO 235
<211> LENGTH: 25
<212> TYPE: DNA
<213> ORGANISM: Human

<400> SEQUENCE: 235
caaacagctt taygaaaagt tttaa 25

<210> SEQ ID NO 236
<211> LENGTH: 25
<212> TYPE: DNA
<213> ORGANISM: Human

<400> SEQUENCE: 236
gtcaggcaat taygagtact aggag 25

<210> SEQ ID NO 237
<211> LENGTH: 25
<212> TYPE: DNA
<213> ORGANISM: Human

<400> SEQUENCE: 237
taatgctatt tcrtactata caact 25

<210> SEQ ID NO 238
<211> LENGTH: 25
<212> TYPE: DNA
<213> ORGANISM: Human

<400> SEQUENCE: 238
gataaccaaa tcrtttttcg gattt 25

<210> SEQ ID NO 239
<211> LENGTH: 25
<212> TYPE: DNA
<213> ORGANISM: Human

<400> SEQUENCE: 239
aaacttaact gcrttctcaa atagt 25

<210> SEQ ID NO 240
<211> LENGTH: 25
<212> TYPE: DNA
<213> ORGANISM: Human

<400> SEQUENCE: 240
gatttgatcc ttrtaaattc catag 25

<210> SEQ ID NO 241
<211> LENGTH: 25
<212> TYPE: DNA
<213> ORGANISM: Human

<400> SEQUENCE: 241
ttgcctttgg gargttcttt gagtt 25

<210> SEQ ID NO 242
<211> LENGTH: 25
<212> TYPE: DNA
<213> ORGANISM: Human

<400> SEQUENCE: 242
tatcctcaaa ttyggtcact caggt 25

<210> SEQ ID NO 243
<211> LENGTH: 25
<212> TYPE: DNA
<213> ORGANISM: Human

<400> SEQUENCE: 243
agcactttgt ttsaatgaaa ctata 25

<210> SEQ ID NO 244
<211> LENGTH: 25
<212> TYPE: DNA
<213> ORGANISM: Human

<400> SEQUENCE: 244
ttcttgtgtc tcmacatttt gtatg 25

<210> SEQ ID NO 245
<211> LENGTH: 25
<212> TYPE: DNA
<213> ORGANISM: Human

<400> SEQUENCE: 245
tattggttca gayactattc gaaat 25

<210> SEQ ID NO 246
<211> LENGTH: 25
<212> TYPE: DNA
<213> ORGANISM: Human

<400> SEQUENCE: 246
caattgcaga gargttttca aatga 25

<210> SEQ ID NO 247
<211> LENGTH: 25
<212> TYPE: DNA
<213> ORGANISM: Human

<400> SEQUENCE: 247
tagatgtgac tgkttcattt agcca 25

<210> SEQ ID NO 248
<211> LENGTH: 25
<212> TYPE: DNA
<213> ORGANISM: Human

<400> SEQUENCE: 248
tgattccacc atyatctata gctcc 25

<210> SEQ ID NO 249
<211> LENGTH: 25
<212> TYPE: DNA
<213> ORGANISM: Human

<400> SEQUENCE: 249
tgggatgtat acygtgagtc actaa 25

<210> SEQ ID NO 250
<211> LENGTH: 25
<212> TYPE: DNA
<213> ORGANISM: Human

<400> SEQUENCE: 250
gagtctacca ttktattggg tacat 25

<210> SEQ ID NO 251
<211> LENGTH: 25
<212> TYPE: DNA
<213> ORGANISM: Human

<400> SEQUENCE: 251
aacttcagaa tarttcaatt accct 25

<210> SEQ ID NO 252
<211> LENGTH: 25
<212> TYPE: DNA
<213> ORGANISM: Human

<400> SEQUENCE: 252
aagtcttttc ctkttgaata ccatc 25

<210> SEQ ID NO 253
<211> LENGTH: 25
<212> TYPE: DNA
<213> ORGANISM: Human

<400> SEQUENCE: 253
acattatggt atraactttg gctgc 25

<210> SEQ ID NO 254
<211> LENGTH: 25
<212> TYPE: DNA
<213> ORGANISM: Human

<400> SEQUENCE: 254
atggcttaat cayaaggaac tacat 25

<210> SEQ ID NO 255
<211> LENGTH: 25
<212> TYPE: DNA
<213> ORGANISM: Human

<400> SEQUENCE: 255
tccctacctg aawcaaccca gtgca 25

<210> SEQ ID NO 256
<211> LENGTH: 25
<212> TYPE: DNA
<213> ORGANISM: Human

<400> SEQUENCE: 256
aactgctaca ttkggagctt tctga 25

<210> SEQ ID NO 257
<211> LENGTH: 25
<212> TYPE: DNA
<213> ORGANISM: Human

<400> SEQUENCE: 257
ggtttgactg ccracgatgc taaga 25

<210> SEQ ID NO 258
<211> LENGTH: 25
<212> TYPE: DNA
<213> ORGANISM: Human

<400> SEQUENCE: 258
tacaaagtag tgyagctgta catca 25

<210> SEQ ID NO 259
<211> LENGTH: 25
<212> TYPE: DNA
<213> ORGANISM: Human

<400> SEQUENCE: 259
tctcaggaga agyggccctt ctgat 25

<210> SEQ ID NO 260
<211> LENGTH: 25
<212> TYPE: DNA
<213> ORGANISM: Human

<400> SEQUENCE: 260
attgcaaact taygatattc acaaa 25

<210> SEQ ID NO 261
<211> LENGTH: 25
<212> TYPE: DNA
<213> ORGANISM: Human

<400> SEQUENCE: 261
gtgcttgcct ccrctctatc gggcg 25

<210> SEQ ID NO 262
<211> LENGTH: 25
<212> TYPE: DNA

<213> ORGANISM: Human

<400> SEQUENCE: 262
gatgcacgat acyagaaata agcat 25

<210> SEQ ID NO 263
<211> LENGTH: 25
<212> TYPE: DNA
<213> ORGANISM: Human

<400> SEQUENCE: 263
atcgccttga taraaatatg atatg 25

<210> SEQ ID NO 264
<211> LENGTH: 25
<212> TYPE: DNA
<213> ORGANISM: Human

<400> SEQUENCE: 264
ctactgcttc atygccctct agtac 25

<210> SEQ ID NO 265
<211> LENGTH: 25
<212> TYPE: DNA
<213> ORGANISM: Human

<400> SEQUENCE: 265
ttgttgtgcg tgkcttggat agcaa 25

<210> SEQ ID NO 266
<211> LENGTH: 25
<212> TYPE: DNA
<213> ORGANISM: Human

<400> SEQUENCE: 266
acctgtgcgt gcraaaccca tggca 25

<210> SEQ ID NO 267
<211> LENGTH: 25
<212> TYPE: DNA
<213> ORGANISM: Human

<400> SEQUENCE: 267
tgcgggacct gcraaaatgt atccc 25

<210> SEQ ID NO 268
<211> LENGTH: 25
<212> TYPE: DNA
<213> ORGANISM: Human

<400> SEQUENCE: 268
gtgtttttaa tcrtagctct ttact 25

<210> SEQ ID NO 269
<211> LENGTH: 25
<212> TYPE: DNA
<213> ORGANISM: Human

<400> SEQUENCE: 269
acagtaacaa tcratcatta tgagc 25

<210> SEQ ID NO 270
<211> LENGTH: 25

<212> TYPE: DNA
<213> ORGANISM: Human

<400> SEQUENCE: 270
tttttacttc ccrtcaaatc acaag 25

<210> SEQ ID NO 271
<211> LENGTH: 25
<212> TYPE: DNA
<213> ORGANISM: Human

<400> SEQUENCE: 271
accattgaga ggktcccctt agcca 25

<210> SEQ ID NO 272
<211> LENGTH: 25
<212> TYPE: DNA
<213> ORGANISM: Human

<400> SEQUENCE: 272
tcttatttta tcygattgaa ttgtg 25

<210> SEQ ID NO 273
<211> LENGTH: 25
<212> TYPE: DNA
<213> ORGANISM: Human

<400> SEQUENCE: 273
atttcgtatt ttraatgccc cacaa 25

<210> SEQ ID NO 274
<211> LENGTH: 25
<212> TYPE: DNA
<213> ORGANISM: Human

<400> SEQUENCE: 274
ccatgaaaga tgrctccaga aactt 25

<210> SEQ ID NO 275
<211> LENGTH: 25
<212> TYPE: DNA
<213> ORGANISM: Human

<400> SEQUENCE: 275
tactgaccgt ccygacgctt tcagt 25

<210> SEQ ID NO 276
<211> LENGTH: 25
<212> TYPE: DNA
<213> ORGANISM: Human

<400> SEQUENCE: 276
actttgtcac atsaaacaag atgag 25

<210> SEQ ID NO 277
<211> LENGTH: 25
<212> TYPE: DNA
<213> ORGANISM: Human

<400> SEQUENCE: 277
ctttgaaaac tgygggatga gttag 25

<210> SEQ ID NO 278

<211> LENGTH: 25
<212> TYPE: DNA
<213> ORGANISM: Human

<400> SEQUENCE: 278
tctgactcaa tcygcctgtc tttag 25

<210> SEQ ID NO 279
<211> LENGTH: 25
<212> TYPE: DNA
<213> ORGANISM: Human

<400> SEQUENCE: 279
caggacacag ctyggggtca cggcg 25

<210> SEQ ID NO 280
<211> LENGTH: 25
<212> TYPE: DNA
<213> ORGANISM: Human

<400> SEQUENCE: 280
ctgtctctac casgtaacac atgac 25

<210> SEQ ID NO 281
<211> LENGTH: 25
<212> TYPE: DNA
<213> ORGANISM: Human

<400> SEQUENCE: 281
ctcggtcttg acrgtctgaa ttact 25

<210> SEQ ID NO 282
<211> LENGTH: 25
<212> TYPE: DNA
<213> ORGANISM: Human

<400> SEQUENCE: 282
tccagacaaa ggratcagtg caagc 25

<210> SEQ ID NO 283
<211> LENGTH: 25
<212> TYPE: DNA
<213> ORGANISM: Human

<400> SEQUENCE: 283
tctcctattt gtyccatggc agtta 25

<210> SEQ ID NO 284
<211> LENGTH: 25
<212> TYPE: DNA
<213> ORGANISM: Human

<400> SEQUENCE: 284
gttactgacg ggmtttagcc attac 25

<210> SEQ ID NO 285
<211> LENGTH: 25
<212> TYPE: DNA
<213> ORGANISM: Human

<400> SEQUENCE: 285
ttacttttca cartctctct aacat 25

<210> SEQ ID NO 286
<211> LENGTH: 25
<212> TYPE: DNA
<213> ORGANISM: Human

<400> SEQUENCE: 286
ggttctgaga gcrccacaag gaaga 25

<210> SEQ ID NO 287
<211> LENGTH: 25
<212> TYPE: DNA
<213> ORGANISM: Human

<400> SEQUENCE: 287
tatcttagcc tastagaatg gaatc 25

<210> SEQ ID NO 288
<211> LENGTH: 25
<212> TYPE: DNA
<213> ORGANISM: Human

<400> SEQUENCE: 288
ttgagggtgt garttttctg tatcc 25

<210> SEQ ID NO 289
<211> LENGTH: 25
<212> TYPE: DNA
<213> ORGANISM: Human

<400> SEQUENCE: 289
tactttgtcc ctstcataga acctg 25

<210> SEQ ID NO 290
<211> LENGTH: 25
<212> TYPE: DNA
<213> ORGANISM: Human

<400> SEQUENCE: 290
gtgcattctt cawactgatt tggga 25

<210> SEQ ID NO 291
<211> LENGTH: 25
<212> TYPE: DNA
<213> ORGANISM: Human

<400> SEQUENCE: 291
agcaggctaa agrtttcact gaagt 25

<210> SEQ ID NO 292
<211> LENGTH: 25
<212> TYPE: DNA
<213> ORGANISM: Human

<400> SEQUENCE: 292
attatcattt gcrtaagcct ctcat 25

<210> SEQ ID NO 293
<211> LENGTH: 25
<212> TYPE: DNA
<213> ORGANISM: Human

<400> SEQUENCE: 293
catacacttc caratcttct gtagc 25

<210> SEQ ID NO 294
<211> LENGTH: 25
<212> TYPE: DNA
<213> ORGANISM: Human

<400> SEQUENCE: 294
aatgataaaa gaygacccat gcctt 25

<210> SEQ ID NO 295
<211> LENGTH: 25
<212> TYPE: DNA
<213> ORGANISM: Human

<400> SEQUENCE: 295
caatctaatg ccrcaagaaa aaata 25

<210> SEQ ID NO 296
<211> LENGTH: 25
<212> TYPE: DNA
<213> ORGANISM: Human

<400> SEQUENCE: 296
tgttattcca acyctgaaca catca 25

<210> SEQ ID NO 297
<211> LENGTH: 25
<212> TYPE: DNA
<213> ORGANISM: Human

<400> SEQUENCE: 297
tgactgagag tartggacac agttt 25

<210> SEQ ID NO 298
<211> LENGTH: 25
<212> TYPE: DNA
<213> ORGANISM: Human

<400> SEQUENCE: 298
gacacgctag acraagggcg tccat 25

<210> SEQ ID NO 299
<211> LENGTH: 25
<212> TYPE: DNA
<213> ORGANISM: Human

<400> SEQUENCE: 299
tgggaatgta atmggcagtt taaga 25

<210> SEQ ID NO 300
<211> LENGTH: 25
<212> TYPE: DNA
<213> ORGANISM: Human

<400> SEQUENCE: 300
gacttgaaaa aayccagact tttga 25

<210> SEQ ID NO 301
<211> LENGTH: 25
<212> TYPE: DNA
<213> ORGANISM: Human

<400> SEQUENCE: 301
agaggaacaa aayggtaagt aatta 25

<210> SEQ ID NO 302
<211> LENGTH: 25
<212> TYPE: DNA
<213> ORGANISM: Human

<400> SEQUENCE: 302
ccaaaactct tayaaattct atggt 25

<210> SEQ ID NO 303
<211> LENGTH: 25
<212> TYPE: DNA
<213> ORGANISM: Human

<400> SEQUENCE: 303
acgaaaatca tamgactcta cggaa 25

<210> SEQ ID NO 304
<211> LENGTH: 25
<212> TYPE: DNA
<213> ORGANISM: Human

<400> SEQUENCE: 304
caaatttcca ctrtcccgag aaggt 25

<210> SEQ ID NO 305
<211> LENGTH: 25
<212> TYPE: DNA
<213> ORGANISM: Human

<400> SEQUENCE: 305
aaagtcattg ttstcaaatg ggatg 25

<210> SEQ ID NO 306
<211> LENGTH: 25
<212> TYPE: DNA
<213> ORGANISM: Human

<400> SEQUENCE: 306
tatctttaag cartttagca agtag 25

<210> SEQ ID NO 307
<211> LENGTH: 25
<212> TYPE: DNA
<213> ORGANISM: Human

<400> SEQUENCE: 307
gatgattaca gtrgtcgtag ttccc 25

<210> SEQ ID NO 308
<211> LENGTH: 25
<212> TYPE: DNA
<213> ORGANISM: Human

<400> SEQUENCE: 308
agtaaatagc tcytttcttt gtaga 25

<210> SEQ ID NO 309
<211> LENGTH: 25
<212> TYPE: DNA
<213> ORGANISM: Human

<400> SEQUENCE: 309

-continued

```
agtccttgaa gartgatcat aaaaa                                      25


<210> SEQ ID NO 310
<211> LENGTH: 25
<212> TYPE: DNA
<213> ORGANISM: Human

<400> SEQUENCE: 310

gcggacctga gtkacctcat ggaac                                      25


<210> SEQ ID NO 311
<211> LENGTH: 25
<212> TYPE: DNA
<213> ORGANISM: Human

<400> SEQUENCE: 311

atcagatgac cargaattga gagac                                      25


<210> SEQ ID NO 312
<211> LENGTH: 25
<212> TYPE: DNA
<213> ORGANISM: Human

<400> SEQUENCE: 312

ctacagaggt acrtgcatag gtcca                                      25


<210> SEQ ID NO 313
<211> LENGTH: 25
<212> TYPE: DNA
<213> ORGANISM: Human

<400> SEQUENCE: 313

tttttctata gayggccagc actgg                                      25
```

METHOD FOR IDENTIFYING MATCHED GROUPS

BACKGROUND OF THE INVENTION

A case control association study may be used to identify genetic markers that are correlated with a phenotypic trait of interest, such as a predisposition to a disease, condition, illness, response to a drug, or other physical characteristic. The most useful and interesting associations are those that are functionally linked to the trait of interest. If case and control groups are not carefully matched to have similar genetic compositions, then studies may find spurious associations that have no causal relationship with the trait of interest.

Association studies have frequently been criticized for their inability to distinguish causal associations from spurious ones due to incomplete matching of cases and controls. Accordingly, further inquiry and analysis are always needed after completing an association study to understand the biological bases of any putative associations, and to determine which are likely to be functionally relevant. Following up on spurious associations can be difficult and expensive.

To reduce the likelihood of spurious associations, some studies have employed homogenous groups of individuals having the same ancestry (ethnicity), in some cases an ethnicity with relatively little genetic variation such as groups from Northern Europe and Iceland. The homogeneity of such groups may reduce the incidence of "false positives," i.e., spurious associations between genetic markers and phenotypes that are in fact due to systematically unequal incidence of genetic markers in case and control groups. However, there are various disadvantages to using homogeneous groups in an association study. For instance, in some homogeneous populations, it may be difficult to find enough individuals with the phenotypic trait of interest, such as a particular disease, or it may be difficult to recruit enough individuals willing to participate in a given study. Additionally, the set of predisposing genetic factors in a restricted population may be less likely to be generalizable to or replicable in other populations. Hence, the usefulness of data derived from these studies may be limited.

Accordingly, nonhomogeneous groups (e.g., groups having a mixture of genetic or ancestral backgrounds) are frequently used in association studies. This mixture can occur as a result of combining individuals of geographically or genetically isolated populations in a study group, and/or having individuals of mixed ancestry in such a group. As indicated, study designs having groups of mixed backgrounds can present difficulties when trying to identify causal associations if the incidence of the phenotype of interest is correlated with genetic loci that are not causally-related to the phenotype of interest but whose correlation is simply due to the unmatched nature of the populations being compared. Association studies have traditionally been designed with only limited attention to matching, often limited to the level of "ethnicity matching" by ascertaining self-reported ethnicities from the participants. This self-categorization may be unreliable and may not accurately reflect the detailed population structure of the groups being studied.

SUMMARY OF THE INVENTION

The techniques of the present invention address a need in the art by providing methods that identify whether groups in an association study are "matched." This is accomplished by comparing distributions of alleles in the groups at various genetic markers. In some preferred embodiments, the methods of the invention are utilized before the association study is conducted. If the distributions vary by more than a statistically acceptable level, one or both groups may be adjusted to bring the distributions into closer agreement.

Thus, one aspect of the invention pertains to methods for identifying matched groups prior to performing a study. Such methods may be characterized by the following sequence of operations: (a) prior to performing a study, identifying members of a control group and members of a case group; (b) for each of a number of selected genetic markers, genotyping a plurality of members in the control group and a plurality of members in the case group; and (c) determining if the groups are matched based on the genotypes of said case group and said control group. In (b) the genotyping identifies a set of alleles corresponding to the genetic markers for each member of the pluralities. Further, the genetic markers are selected to identify differences in population structure between members.

The invention may employ various methods and reagents for efficiently genotyping a plurality of individual samples for a plurality of biallelic genetic markers that have been selected for identification of population structure differences among members of a study population that are unrelated to a phenotypic trait of interest. One such method may be characterized by the following sequence: (a) PCR amplification of DNA samples in an optimized multiplex format; (b) fragmentation and fluorescent labelling of the amplified DNA products; (c) hybridization of the labelled products to oligonucleotide arrays designed for genotyping of diploid genetic material; and (d) analysis of fluorescence intensity data to determine individual marker genotypes.

Another aspect of this invention pertains to methods for analysis of genotype data from a plurality of markers, to determine whether an association study is at risk for finding spurious associations due to population structure. If corrective action is required, the same methods can be used to ascertain whether the corrections to the composition of the case and control populations are sufficient to reduce the incidence of spurious associations to a nominal level. The methods are of particular application to association studies that employ pooled genotyping, because detection of and correction for population structure must be done prior to pooling.

Another aspect of this invention pertains to methods for selecting matched case and control groups in an association study, using population structure information inferred from genotype data for a plurality of genetic markers. One variation involves selection of members of case and control groups to have the same proportions of individuals from a series of groups having relatively similar genetic backgrounds. Another variant involves selection of cases and controls to have the same over-all proportional representation of their ancestral populations, without requiring similar distributions for the individuals composing the groups. A third variant involves adjusting a measured quantitative phenotype to account for population structure differences, and then defining case and control groups based on the adjusted phenotype.

Yet another aspect of the invention pertains to computer program products including machine-readable media on which are provided program instructions for implementing the methods described above, in whole or in part. Frequently, the program instructions are provided as code for performing certain method operations. In addition, the invention pertains to various combinations and arrangements of data generated and/or used as described herein.

These and other features and advantages of the present invention will be described in more detail below with reference to the associated figures.

BRIEF DESCRIPTION OF THE DRAWINGS

The techniques of the present invention may be understood by reference to the following description taken in conjunction with the accompanying drawing figures, in which like parts may be referred to by like numerals.

FIG. 4 is an exemplary table showing allele counts and association test statistics in case and control groups.

FIG. 6 is an exemplary table showing the distribution of expected and observed p-values for tests of association of individual loci with a phenotype.

FIG. 7A is an exemplary stratification table for case and control groups.

FIG. 7B is an adjusted version of the exemplary stratification table for case and control groups.

DETAILED DESCRIPTION OF INVENTION

Figure 1:
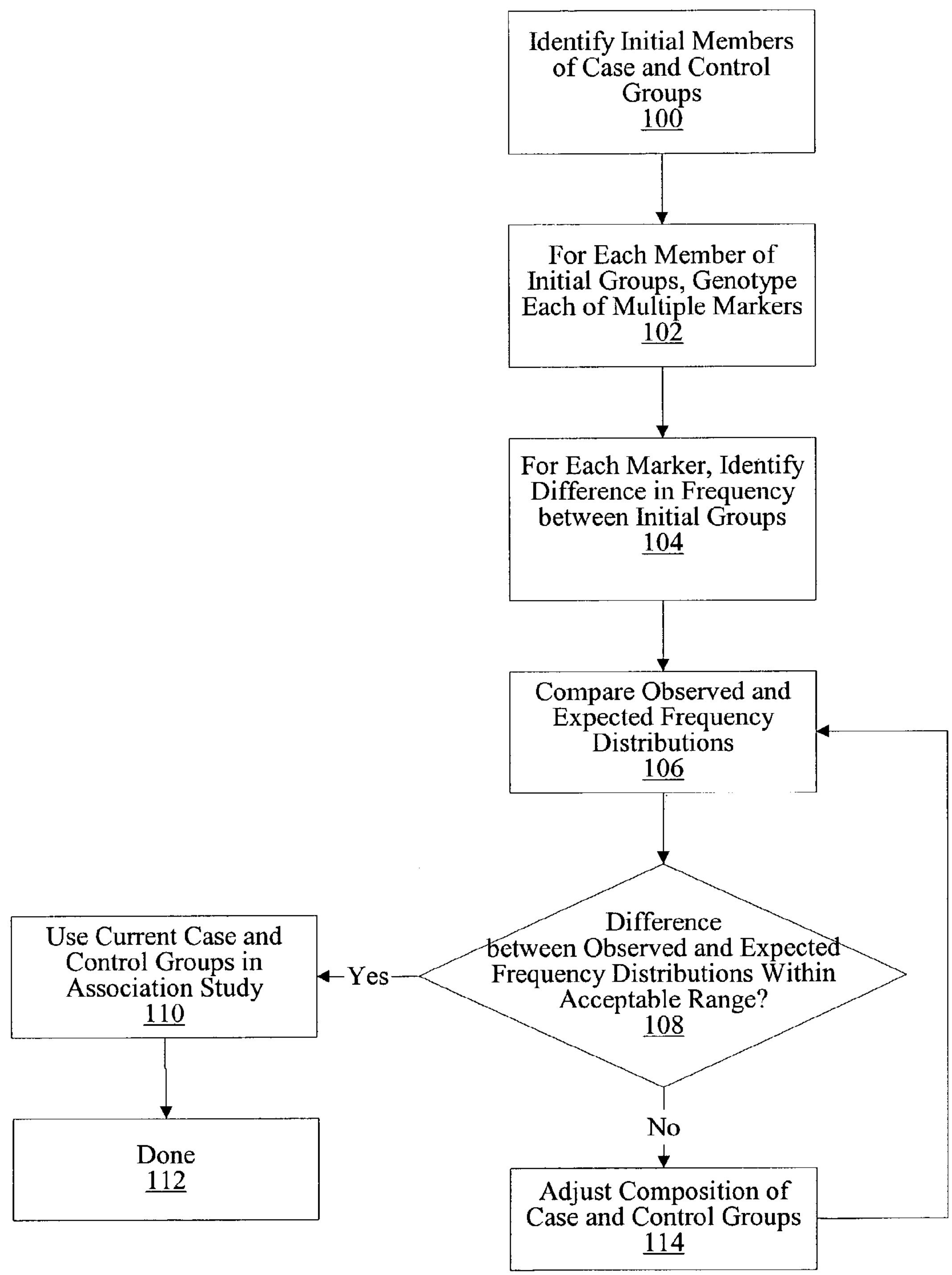
FIG. 1 is a process flow diagram illustrating an exemplary process for identifying and creating groups with matched compositions.

Association studies may be used to identify genetic markers that are correlated with a phenotypic trait, such as a predisposition to a disease, a chronic condition, illness, or other physical characteristic. A major challenge in carrying out these kinds of studies is to determine whether observed correlations between markers and traits have a causal basis. In an ideal association study, the only genetic differences between the case and control groups would be the loci that are causally-related to the phenotypic trait of interest, i.e., their population structures would be nearly identical. Population structure refers to the heterogeneity and genetic composition of individuals within a population. Although this strategy may be applicable to highly inbred organisms, such as laboratory mice, this is not possible in human populations due to the vast amounts of variation between individuals, much of it relating to ethnicity or ancestral heritage, and not to the trait of interest. Some association studies attempt to control for this variation, but "ethnicity matching" by ascertaining self-reported ethnicities from the participants is unreliable and may not accurately reflect the population structure of the groups being studied. Many individuals may not be able to provide an accurate account of their ethnic heritage, especially in North and South America, where immigration and ethnic mixing have been extensive and extend over significant numbers of generations. As indicated, other studies attempt to get around this issue by using homogeneous populations in association studies, but this strategy limits the study design and the usefulness of the data produced in various undesirable ways. For example, the size of the case and control populations may be limited and the set of predisposing genetic factors in a restricted population may be less likely to be generalizable to or replicable in other populations.

Thus, to find the set of predisposing factors that are most applicable to the greatest number of individuals outside of the study populations, a nonhomologous population is desired. However, with that kind of population comes an increased risk of identifying spurious associations, or "false positives". Hence, the population structure of case and control groups must be balanced, or "matched" in order to increase the likelihood that correlations identified in a study stem from a causal relationship between a genetic locus and a phenotypic trait of interest. If the case and control groups of an association study are genetically unbalanced in some regard, aside from the phenotypic trait of interest, then the imbalance may be incorrectly associated with the trait of interest, generating a false positive. Therefore, what is needed is a way to measure and control for the population structure of nonhomologous populations.

As an example, consider a case group biased toward European ancestry in a study on prostate cancer. A researcher considering alleles that are more common in the case group than the control group may falsely conclude that some such alleles are functionally linked with the phenotype of interest, prostate cancer, when in fact they are correlated with European ethnicity. If the case and control groups are genetically unbalanced in any way other than in the phenotype of interest, one cannot safely determine which markers are causally related to the phenotypic trait of interest.

To further illustrate this point, consider an association study intended to identify markers related to hypertension, in which two groups of individuals are compared: one group having hypertension (the case group) and the other without hypertension (the control group). The members of the groups have been surveyed in an attempt to balance phenotypic traits other than hypertension, and are all of Western European ancestry. Further, the researchers chose certain genetic markers for comparison between the two groups. These may be selected to fall in candidate regions suspected of having a role in the phenotype of interest, or may be selected without regard to a specific prior hypothesis regarding their biological function. Regardless, the allelic differences between individuals in the groups are identified at the various markers chosen for study. A particular allele or group of alleles may appear to correlate with the individuals having hypertension. However, upon further inquiry, it is discovered that the group having hypertension includes a higher proportion of individuals with Italian ancestry. This may have occurred because of a defect in how the case and control groups were ascertained or because individuals with Italian ancestry tend to have a high incidence of hypertension, possibly as a result of environmental influences.

Either way, this ethnic mismatch between the two groups in the association study may lead researchers to incorrectly conclude that an allele associated with Italian ancestry is causally associated with hypertension. Researchers will not be able to distinguish which of the identified markers might generally be associated with Italian ancestry and which of the markers might generally be associated with hypertension, because these outcomes are confounded in this study population. Accordingly, further inquiry and analysis is needed to determine which of the genetic markers relate to hypertension.

Instead, had the two groups been matched before the association study was conducted, the confounding population structures of the case and control groups could have been corrected, saving much time, effort, and expense. If the two groups had approximately equal degrees of Italian ancestry, then markers associated with Italian ancestry would be unlikely to show up as differences in allele frequencies between the two groups. One way of determining the ancestral make-up of a group of individuals before conducting an association study is to ask the individuals in a survey. However, as previously described this method is unreliable for measuring population structure in a study group. Accordingly, more accurate methods of identifying matched groups before conducting an association study are desirable.

The techniques of the present invention address the above issues and needs by measuring the population structure of groups to identify matched groups before conducting an association study. More particularly, according to various embodiments, two groups of individuals are chosen and genotyped for a relatively large group of genetic markers (e.g., 100 or more). Using the results of this genotyping, differences in population structure between the groups are identified based on statistically significant differences in allele frequencies between the two groups. Using the information contained in these differences, the groups are adjusted until they are matched. When the groups are matched, they are ready for use in an association study.

Turning now to FIG. 1, an exemplary process is depicted for comparing the population structures of two or more groups and for balancing such groups to produce modified groups having more matched compositions. At 100, individuals selected to participate in an association study are identified as initial members of case and control groups, respectively. Members of the case group are chosen because they exhibit the phenotype of interest, such as a predisposition to a disease, condition, illness, a particular response to a drug, or other physical characteristic. Members of the control group are chosen because they lack the phenotype of interest. In other situations, case and control groups may be defined as ranges of values of a quantitative trait. For example, a "low cholesterol" control group may be comprised of individuals whose total blood cholesterol count is 200 mg/dL or less, while the "high cholesterol" case group may be comprised of individuals whose total blood cholesterol count is greater than 200 mg/dL.

Next, at 102, individuals in the case and control groups are genotyped using a set of genetic markers chosen to indicate differences in population structure. Various types of genetic markers can be used for this purpose. Examples include multi-allelic single nucleotide polymorphisms ("SNPs"), microsatellites, and the like. The markers preferably are sufficiently far apart that they do not exhibit significant linkage disequilibrium. Preferably, the markers will be substantially uniformly distributed across the genome. Generally, the method should employ 100 or more, and even more preferably about 300 or more. In one implementation of this invention, 312 SNPs were used to genotype each of the individuals, as described in more detail below with regard to FIG. 2.

Each genetic marker is found at a particular region (or "locus") of interest in a genomic sequence. For an individual locus on a single strand of DNA, only one of a plurality of alleles is present, and is characterized by the nucleotide sequence at that locus. For example, bi-allelic SNPs have only two alleles; so, at a given bi-allelic SNP locus on a single strand of DNA, only one of two alleles (i.e., adenine ("A"), thymine ("T"), guanine ("G"), or cytosine ("C")) will be present. In certain preferred embodiments, bialleleic SNPs are used, and in more preferred embodiments these SNPs are common SNPs (SNPs that have a minor allele frequency of at least 10%). Further, although the examples provided herein will primarily discuss detection of SNPs in DNA, SNPs may also be detected in DNA derivatives, such as RNA or cDNA, and the like, as will be clear to those of skill it the art.

For the sake of convenience in this description of the techniques of the present invention, the two alleles of a bi-allelic marker (e.g., a bi-allelic SNP) will be arbitrarily referred to as X and Y, regardless of which of the actual alleles characterize that particular genetic marker. For example, a SNP marker may have A and G as alleles. For convenience, these will be referenced as binary values X and Y. The same would be true for a different SNP marker, where the two alleles are C and T, A and T, G and C, G and T, or A and C.

Understand that SNPs are not the only types of marker that can be used. Any stable genetic feature having alleles that are differentially distributed across populations can be used. One example already mentioned is a microsatellite, which is a sequence of highly variable length that contains di- or tri-nucleotide repeats. Microsatellites can repeat for any number of times. For example, a microsatellite having the following sequence, ATGATGATG (SEQ ID NO:1), is three bases long and repeats three times. Even when a given microsatellite is present on multiple chromosomes in an individual, it may vary in the number of repeats present on each chromosome. For example, ATG microsatellite may repeat 3 times in some chromosomes, 5 times in others, and 8 times in still others. Hence the number of repeats in a particular microsatellite can serve as a genetic marker in accordance with this invention. Other markers that could be used include VNTRs (variable number of tandem repeats), STRs (short tandem repeats), RFLPs (restriction fragment length polymorphisms), insertions, deletions and the like.

Each individual is genotyped to provide two allele values (one for each chromosome) for each of the genetic markers. Genotyping can be conducted by any reliable, efficient method for distinguishing the possible alleles. Note that individuals have two copies of every chromosome. So they have two copies of each marker, which means that they have two allele values for each marker. As a consequence, the genotyping procedure will identify two allele values for each individual. As described in more detail below with regard to FIG. 2, genotyping can be conducted by applying a DNA sample to a DNA array to determine which alleles the individual has for each of the genetic markers. Such arrays are commercially available from, e.g., Affymetrix, Inc., (Santa Clara, Calif.). Of course, other methods are also suitable; for example, direct sequencing of the regions encoding each marker.

After collecting the individual genotypes, the distributions of alleles in cases and controls can be compared with the distributions expected if the same numbers of cases and controls were randomly selected from one homogeneous population. As illustrated at blocks 104 and 106 of FIG. 1, a typical procedure characterizes each marker by a difference in allele frequency between the case and control groups. It compares this information with expected values to draw a conclusion about how well the groups match. Several such methods are available and should be familiar to those skilled in the art. These methods rely on the expectation that few or none of the markers selected for the stratification analysis are likely to have any functional association with the phenotype used to define cases and controls, so any evidence for associations in these few markers is evidence that cases and controls are inadequately matched.

One such method is to perform, for each marker, a chi squared test of independence of the individual allele counts in cases and controls. Each such test produces a score statistic, and the set of score statistics for all markers should conform to a chi squared distribution with one degree of freedom. A "Q—Q" plot of the ordered scores against corresponding chi squared quantiles should have a slope of 1 in the situation where cases and controls are well matched, and gives a simple visual interpretation of the quality of fit between the expected and observed distributions. Q—Q plots are known to those of skill in the art. See Wilk, M. B. and Gnanadesikan, R. (1968) "Probability plotting methods for the analysis of data", *Biometrika* 55:1–17, which is incorporated herein by reference in its entirety for all purposes.

A closely related method involves calculating, for each marker, a "p-value" representing the probability of observing as extreme a chi squared statistic as the observed one by chance, assuming that the marker is not associated with the phenotype. It is expected that, assuming cases and controls are well matched, 10% of the markers selected for the stratification analysis should exhibit p-values of 0.1 or lower; 1% of the markers should exhibit p-values of 0.01 or lower; and so on. An excess of markers that exhibit small p-values hence indicates that the case and control groups are not matched. The use of p-values and chi squared statistics are known to one of skill in the art and are described in greater detail in Bevington, P. R. and Robinson, D. K., *Data Reduction* and *Error Analysis for the Physical Sciences*, Second Edition, McGraw-Hill, Inc., 1992.

A third related method exploits a property that the sum of the chi squared statistics for N individual markers should follow a chi squared distribution with N degrees of freedom. This method allows determination of an overall ("global") p-value for the complete set of markers. The global p-value gives the probability of seeing a similarly extreme set of chi squared statistics assuming that the groups are matched. Thus, the groups are determined to be matched if the p-value exceeds an acceptable threshold. An acceptable threshold is typically dependent on the desired level of population structure similarities between groups in a particular study. For example, a higher threshold would require a higher degree of similarity between the population structures of the groups as compared to a lower threshold. This method is of limited utility, however, because given a sufficiently large number of markers, fairly small differences between cases and controls could give impressively small p-values even though these differences would be unlikely to result in large numbers of spurious associations. Further description of the global p-value test is described in Prichard, J. K. and Rosenberg, N. A. (1999) "Use of unlinked genetic markers to detect population stratification in association studies", Am. J. Hum. Genet. 65:220–228, which is incorporated herein by reference in its entirety for all purposes.

Using a technique such as one of those identified above, the process determines whether a difference between observed and expected differences in measured allele frequencies is "acceptable." See decision 108. If it is determined that the allelic differences between cases and controls are inconsistent with the hypothesis of a homogeneous population, and the differences are sufficiently large that the study is anticipated to produce unacceptable numbers of spurious associations, then at 114, the case and control groups can be adjusted to provide better matching. The adjusted groups can then be tested in silico using the already collected genotype data at 106, to see if the adjustment is sufficient to reduce the expected numbers of spurious associations. This process continues until the population structures of the case and control groups are matched to the degree required at 108, at which point the process continues to its conclusion at block 112, typically via performance of an association study as indicated at block 110. Although FIG. 1 is shown with a specific sequence, it should be recognized that portions of the sequence can be combined or rearranged without departing from the present invention. For instance, 104 and 106 can be combined in some embodiments. Furthermore, 114 can be followed by 104, or even 102 if new members are added to the groups, instead of 106 in some embodiments. And, as indicated, after the groups are matched, then these matched groups can be used in an association study at 110 to identify markers that correlate with a phenotypic trait of interest. Association studies may be performed by many methods known in the art. Specific descriptions of preferred embodiments are disclosed in U.S. patent application Ser. No. 10/106,097, filed Mar. 26, 2002, entitled "Methods for Genomic Analysis", which is incorporated herein in its entirety for all purposes.

Figure 2:
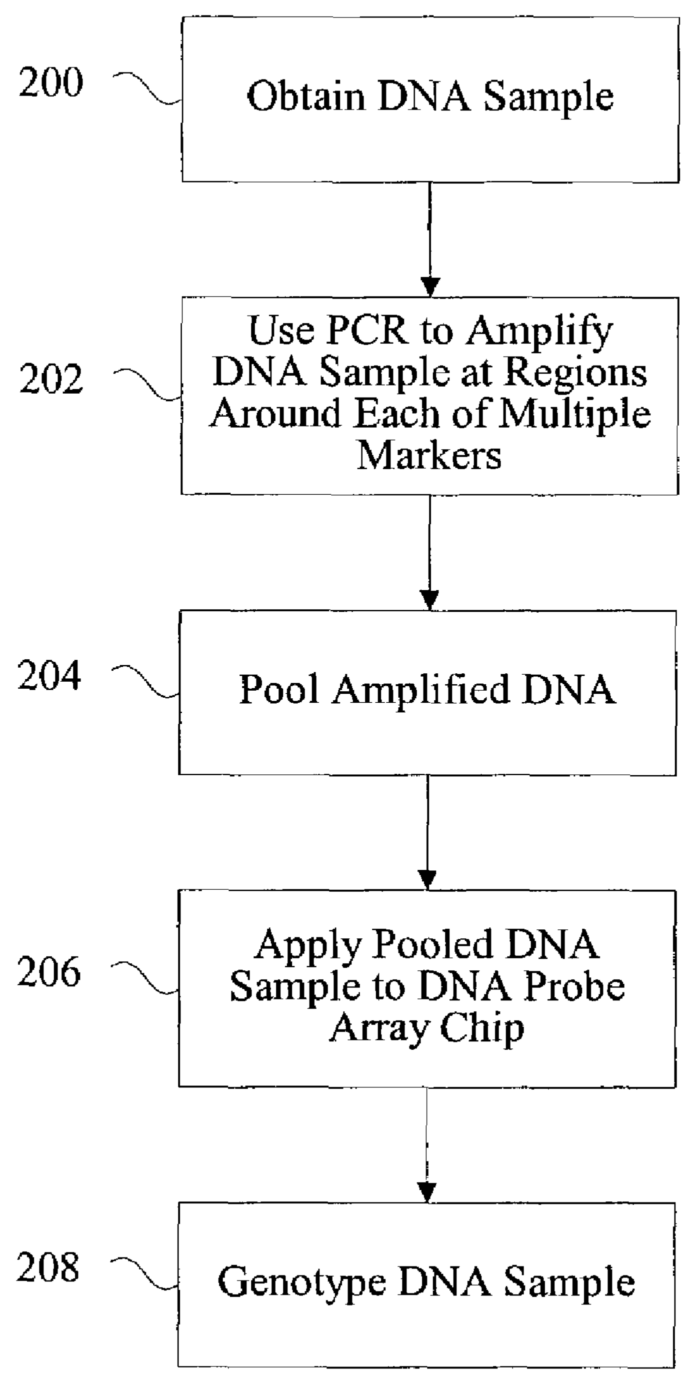
FIG. 2 is a process flow diagram illustrating an exemplary process for genotyping an individual.

With reference now to FIG. 2, an exemplary process for genotyping an individual is shown. This process may correspond to operation 102 of FIG. 1. As a prelude to the FIG. 2 genotyping process, the researchers must identify a group of genetic markers to be used as described above. These are the markers used in the genotyping methodology of FIG. 2. Fundamentally, the markers should come from unlinked genetic loci. Otherwise some of the markers would provide no additional information beyond that provided by a linked counterpart. And there should be a sufficient number of them to provide a trustworthy representation of population structure. Preferably, as indicated above, there are at least about 20 such genetic markers, more preferably between about 100–1000, more preferably between about 200–500, and even more preferably, at least about 300.

One set of criteria for choosing markers that has proven useful includes the following. First, the markers should be polymorphic across widely diverse populations, for example, those comprised of individuals from different ethnicities, geographic locations and ancestral backgrounds, such as individuals from African, Asian, European, Native South American, and Native North American ancestries. In other words, various alleles for a given marker should be present in a wide range of different populations. So, in this approach, the different alleles of a marker should be polymorphic across a group of individuals having widely varying ethnic backgrounds. For example, for a biallelic SNP, both alleles should be present in most of the world's populations, but the allele frequencies may vary widely. In fact, it is desirable to choose markers whose allele frequency is variable across different populations. Second, the markers should be separated from one another by a sufficiently large distance, so that they are unlikely to be correlated, or "linked", with each other. The haplotype structure of the human genome indicates that strong correlations exist on scales of 10 to 100 kilobases. A spacing of at least about 5 megabases, preferably at least about 8 megabases, and more preferably at least about 10 megabases is sufficient to minimize these correlations.

Third, the markers are preferably chosen to perform well in the physical technique employed to identify alleles (i.e., genotype). Genotyping techniques may utilize enzymatic, electrophoretic, chromatographic, or physical methods for discriminating allelic variants. For example, allele-specific PCR, allele-specific single-base primer extension, allele-specific ligation, allele-specific enzymatic cleavage, or nucleotide analogs (e.g., peptide nucleic acids and locked nucleic acids) may be used to discriminate between alternative alleles at a genetic locus. Detection methods for genotyping may involve, for example, fluorescence detection, fluorescence resonance energy transfer, fluorescence polarization, electrochemical detection, mass spectrometry, or atomic force microscopy. Genotyping may be carried out in solution or on a substrate, which includes but is not limited to oligonucleotide chips or bead arrays. So, if for example, the techniques employs DNA microarrays, DNA samples containing the chosen markers should hybridize well with a probe array on a DNA probe array chip or DNA probe array wafer. If the technique employs PCR amplification of nucleic acids, the markers should amplify reliably. Other techniques that may be used to genotype the markers include, but are not limited to, "Taqman" kits (Applied Biosystems (Foster City, Calif.)), "Invader" genotyping products (Third Wave Technologies (Madison, Wis.)), "the MassARRAY system" (Sequenom (San Diego, Calif.)), and the like.

In one example, SNPs were selected as genetic markers using the following procedure. First a full set of approximately 1.7 million known human SNPs, identified by Perlegen Sciences, Inc. of Mountain View, Calif., were considered. From this set, SNPs near "contig boundaries" or known repetitive elements (within approximately 150 base pairs) were eliminated from consideration. This was done for the purpose of increasing the probability of designing appropriate PCR primers for the SNP. Contig boundaries resulted from the process employed to sequence the human genome. They represent boundaries between separate sequences mapped in the process and they may be unreliable. Repeat units can be identified by publicly available programs such as RepeatMasker. Obviously, reliable amplification with PCR is difficult in cases where the amplicon is located near repeat units.

To ensure that the markers are well represented across diverse populations, a group of individuals of diverse ancestry were genotyped. Twenty chromosomes were considered from this globally diverse panel. The allele frequency of SNPs remaining after contig/repeat filtering was considered. The process eliminated SNPs having fewer than 8 calls (out of 20) for either allele. So preferably biallelic genetic markers have allele frequencies of between about 40 and 60 percent across a widely varied population.

Optionally, SNPs near a haplotype block boundary may be eliminated from consideration. For example, in certain embodiments, any SNP not more than 2 SNPs away from a haplotype block boundary may be eliminated. This may reduce the odds that a selected SNP will behave differently from other SNPs in its vicinity and increase the probability that a selected SNP will exhibit behavior that is consistent with the SNPs in its vicinity.

Using the surviving SNPs, the inventors calculated a score based on three criteria: the estimated allele frequency, the rate at which they could reliably identify the allele of a particular SNP on SNP discovery probe arrays ("strict call rate"), and the average conformance of long range PCR amplicons on the arrays. More specifically, the strict call rate is the fraction of SNP discovery probe arrays for which the forward and reverse tilings of the SNP both yielded the same allele determination with a very high confidence level. Conformance is a measure of the fraction of base calls that match a reference sequence. Particular embodiments of forward and reverse tilings for SNPs and methods for calculating conformance are detailed in patent applications U.S. Ser. No. 60/460,329, filed Apr. 3, 2003, entitled "Apparatus and Methods for Analyzing and Characterizing Nucleic Acid Sequences", and U.S. Ser. No. 10/351,973, filed Jan. 27, 2003, entitled "Apparatus and Methods for Determining Individual Genotypes", both of which are incorporated herein by reference for all purposes. For the allele frequencies, the score gave better ranks to SNPs that were closer to a frequency of 50 percent. The strict call rate was a test for good hybridization properties of the sequence containing the SNP itself. The conformance test was a measure of both PCR success and overall quality of hybridization across the region of the containing the SNP. The formula for the score was the following:

Score=0.25*[1−2*abs(freq-0.5)+2*calls/scans+avg-conf]

The score varies from 0 to 1, with a value of 1 being perfect. Initially, the inventors discarded all SNPs with scores of less than 0.70.

For the remaining SNPs, for each chromosome, starting at a position of 1 Mbase, the inventors picked the highest scoring SNP within +/−1 Mbase of that position. From there, they added 9 Mbase, and again picked the best SNP within +/−1 Mbase, and so on. At the end of the process, 312 genetic markers were obtained.

In a specific example, the above selection criteria were used to choose 312 genetic markers. These were then used to identify differences in population structure between case and control groups. The 312 SNPs are included in Table 1. As shown, the SNPs are uniquely identified by a SNP number (sequentially chosen from 1–312), a chromosome number identifying the human chromosome on which the SNP is located, reference and alternate bases for the SNP (which identify the exact allelic values), and the 25mer sequence bracketing the SNP displayed in the conventional 5' to 3' orientation for nucleic acids (with the SNP being at position 13).

TABLE 1

| SNP | CHROMOSOME | REF_ BASE | ALT_ BASE | 25MER | Sequence Indentifier |
|---|---|---|---|---|---|
| 1 | 1 | g | c | TACCATCATTTTNGAATTGTTCAGA | SEQ ID NO:2 |
| 2 | 1 | c | t | GGCCTAGAGTTANGGCATTTCACTT | SEQ ID NO:3 |
| 3 | 1 | c | t | GAGAGTTCAATGNGTAAAGATGCCC | SEQ ID NO:4 |
| 4 | 1 | t | c | TAATTGGGGTTTNGTAACTAGCTAC | SEQ ID NO:5 |

TABLE 1-continued

| SNP | CHROMOSOME | REF_ BASE | ALT_ BASE | 25MER | Sequence Indentifier |
|---|---|---|---|---|---|
| 5 | 1 | a | g | CAATTGCTCATCNAGTCCATGAAAG | SEQ ID NO:6 |
| 6 | 1 | t | c | GGTACGCTTCAANGTTATATGCGGT | SEQ ID NO:7 |
| 7 | 1 | c | t | GAGATCTCAAACNTTAATTTTACTG | SEQ ID NO:8 |
| 8 | 1 | g | c | CAAGCTGAACCTNAATGTAGCTCCA | SEQ ID NO:9 |
| 9 | 1 | a | t | GTGTCCCACTATNTAAGAAATGTTT | SEQ ID NO:10 |
| 10 | 1 | g | a | TTAACCGTCTGTNCTCTCTACACGG | SEQ ID NO:11 |
| 11 | 1 | a | t | TATATCCAACCANCTCTTGGCTCTA | SEQ ID NO:12 |
| 12 | 1 | c | a | CGTAGGCCGTAANCTGATGCCATGA | SEQ ID NO:13 |
| 13 | 1 | g | c | CTTACTTTTCACNTTACTACTTGCA | SEQ ID NO:14 |
| 14 | 1 | g | t | TGAGTTATAGAGNTGAATCCATGTG | SEQ ID NO:15 |
| 15 | 1 | a | c | GAAAACCATTCTNAATTCCAGTTCC | SEQ ID NO:16 |
| 16 | 1 | g | a | CTAGGAGCTACANATAGTTCCAACC | SEQ ID NO:17 |
| 17 | 1 | c | g | CAATGGGAGATTNAGGCCTAGAGCA | SEQ ID NO:18 |
| 18 | 1 | a | g | AAGGTACATATTNGGATGAGATACT | SEQ ID NO:19 |
| 19 | 1 | t | c | TTGATAATTTGANTAAAGCTGACCT | SEQ ID NO:20 |
| 20 | 1 | c | t | ACTGGCTGCGCANGGACAAGTGTCA | SEQ ID NO:21 |
| 21 | 1 | c | t | TCATTCTTACCANTGGTGCTGAAAA | SEQ ID NO:22 |
| 22 | 1 | a | g | ATTTTTCAGCTTNATTTAACATTGT | SEQ ID NO:23 |
| 23 | 1 | t | c | TAATCTTTATTGNATTCTCATTGGC | SEQ ID NO:24 |
| 24 | 1 | c | a | GACAGTCTGCAANAAAATTTTCTGG | SEQ ID NO:25 |
| 25 | 1 | g | a | TTTACCAGGTCCNCCAAGACTATGA | SEQ ID NO:26 |
| 26 | 1 | g | a | TCACACAAAGGCNTAATCATGAAAA | SEQ ID NO:27 |
| 27 | 1 | g | a | GGAATTGTGCTANATACAAAAATGC | SEQ ID NO:28 |
| 28 | 2 | t | c | ACAGAAGTTAAGNTAAACGTTCTAA | SEQ ID NO:29 |
| 29 | 2 | g | a | AATAACTTCCGCNTAATGAGTACCC | SEQ ID NO:30 |
| 30 | 2 | c | g | CTGGCTTCAGAANTGATCTTTTCCT | SEQ ID NO:31 |
| 31 | 2 | a | g | GTATTTGTCTGANTCATAGAATTTA | SEQ ID NO:32 |
| 32 | 2 | a | g | CAAGTCACATCANGAAGTTGTGGGC | SEQ ID NO:33 |
| 33 | 2 | t | a | AACGGAACAATANTACATTCCTGGG | SEQ ID NO:34 |
| 34 | 2 | a | c | ATAAGCAGCCATNTTATTGAGAAGC | SEQ ID NO:35 |
| 35 | 2 | g | a | TAACAAACATAANATTTGCATTATA | SEQ ID NO:36 |
| 36 | 2 | g | a | TAAGGAGCTAATNGCCAATAATTAC | SEQ ID NO:37 |
| 37 | 2 | a | g | GGCAGGGAACCANTCTTTAGAAACT | SEQ ID NO:38 |
| 38 | 2 | g | a | TTCAAGGAACCCNTGTTGATAATAA | SEQ ID NO:39 |
| 39 | 2 | t | c | TTATACTACAGANGTTCATTATGCC | SEQ ID NO:40 |
| 40 | 2 | g | a | GCAGAATGCCCCNTCCGTAAATGTC | SEQ ID NO:41 |
| 41 | 2 | a | g | TTTGAATCAGAGNAGTGATTTTGAA | SEQ ID NO:42 |
| 42 | 2 | a | c | TCTGCGATCTGGNAATAGAGCTTTC | SEQ ID NO:43 |

TABLE 1-continued

| SNP | CHROMOSOME | REF_ BASE | ALT_ BASE | 25MER | Sequence Indentifier |
|---|---|---|---|---|---|
| 43 | 2 | t | c | ATACCTCTCCAGNCACACATAATAA | SEQ ID NO:44 |
| 44 | 2 | g | a | AGTAATCACTTTNTGTCAAAATGTT | SEQ ID NO:45 |
| 45 | 2 | a | g | TCACTAGATGCANATTTCTTCATGT | SEQ ID NO:46 |
| 46 | 2 | g | a | AATTTCAGCAGANGGATTATGATGC | SEQ ID NO:47 |
| 47 | 2 | g | a | TAAAATTTTCCANGCTGGAGCAATT | SEQ ID NO:48 |
| 48 | 2 | a | t | AACAATCGAGGTNGGCTTTAAAGGA | SEQ ID NO:49 |
| 49 | 2 | c | t | GTTAGCACAGTTNATAGCAAGTCTT | SEQ ID NO:50 |
| 50 | 2 | a | g | ATTGCTTGGCACNTTCTCAGAGGTG | SEQ ID NO:51 |
| 51 | 2 | g | a | CGCTTCTTGCAGNGGAACTTCATGG | SEQ ID NO:52 |
| 52 | 2 | a | g | ACCATGTTGAGANTTGTGCCTAGCT | SEQ ID NO:53 |
| 53 | 2 | c | g | GCAGACCAGAGANTGTCAATTTAAG | SEQ ID NO:54 |
| 54 | 2 | g | a | ACATCTTAATGANGTGCTGACATTT | SEQ ID NO:55 |
| 55 | 3 | a | g | CTGATATAGGCCNTAGTGTCAGGAC | SEQ ID NO:56 |
| 56 | 3 | g | a | CATGAGATGGCCNTTTTCCAGGAGA | SEQ ID NO:57 |
| 57 | 3 | t | c | ATAACATCCTGCNGGTTACTGATCA | SEQ ID NO:58 |
| 58 | 3 | g | a | CCCTGGGAACACNCTACTGAGAGCC | SEQ ID NO:59 |
| 59 | 3 | c | g | TACTATGGGGAANAACTTGTCACTT | SEQ ID NO:60 |
| 60 | 3 | t | c | AACTTACTGGAANGGGAACTTTTCA | SEQ ID NO:61 |
| 61 | 3 | t | c | GATACCCTTATANGGCAGAACTTTA | SEQ ID NO:62 |
| 62 | 3 | t | a | CTGTTGGGAAACNCTTCAGTCACAC | SEQ ID NO:63 |
| 63 | 3 | g | a | GGGTACAATTAGNTCTTACTCATGC | SEQ ID NO:64 |
| 64 | 3 | c | t | CAATTTCGTACANTTGAAAGAGACA | SEQ ID NO:65 |
| 65 | 3 | c | t | GCCTTACAGAGCNGTGATTTTGGCT | SEQ ID NO:66 |
| 66 | 3 | a | g | AATCCTGACGGTNGGTTCTACAATT | SEQ ID NO:67 |
| 67 | 3 | t | c | TTTCAAGAGGTGNGAGGACAAGGCC | SEQ ID NO:68 |
| 68 | 3 | a | g | CATTCCTGGCTGNTCGTAGACAAGG | SEQ ID NO:69 |
| 69 | 3 | a | g | GAATCAGAAGGCNAAATGTTTGGGC | SEQ ID NO:70 |
| 70 | 3 | c | g | AACGTGGAACAANAGTGAAAAAATG | SEQ ID NO:71 |
| 71 | 3 | a | g | GTGTTTACTCCANAATACCAGCTTA | SEQ ID NO:72 |
| 72 | 3 | a | g | AAAGGGTCAGTCNTTGAAACATTGC | SEQ ID NO:73 |
| 73 | 3 | a | g | CCAGTGCCCGGCNAGTAACCAACGC | SEQ ID NO:74 |
| 74 | 3 | t | c | AAGTGTGCATAANGTAGAGACTCAT | SEQ ID NO:75 |
| 75 | 3 | g | a | TGACTTTAGAGCNTAGTATTTTAGC | SEQ ID NO:76 |
| 76 | 3 | c | t | TAGGTGGCAAATNGATACCCTGAGG | SEQ ID NO:77 |
| 77 | 3 | c | a | TGATTTTTGGATNGGAAAGGAGACT | SEQ ID NO:78 |
| 78 | 3 | g | c | GCGAGGACCTATNGGATGTGTAGGC | SEQ ID NO:79 |
| 79 | 3 | g | a | CATGGCGCTTTANCACAAGTATGGA | SEQ ID NO:80 |
| 80 | 4 | g | c | TCTGAAACCATCNCAGGAATGATGC | SEQ ID NO:81 |

TABLE 1-continued

| SNP | CHROMOSOME | REF_ BASE | ALT_ BASE | 25MER | Sequence Indentifier |
|---|---|---|---|---|---|
| 81 | 4 | t | c | TTCTAGTCTCCTNCCCGGGCGGTCA | SEQ ID NO:82 |
| 82 | 4 | a | c | GCTGAGAATTTCNAGTGTGATCGGT | SEQ ID NO:83 |
| 83 | 4 | c | t | TGGTTTCTTGCANTGGGAGGGAGAC | SEQ ID NO:84 |
| 84 | 4 | c | t | TATGTAAAAGCANGTGTCATTATGA | SEQ ID NO:85 |
| 85 | 4 | t | c | TCACATTTTCTTNCAAAGGCAAGTA | SEQ ID NO:86 |
| 86 | 4 | t | g | TTACTGAACAAANTATCATCTCAGG | SEQ ID NO:87 |
| 87 | 4 | c | t | TGAATAATGCCTNTAGGGTCTGAAT | SEQ ID NO:88 |
| 88 | 4 | t | c | CACTTTACGGCTNTCACCATTCACA | SEQ ID NO:89 |
| 89 | 4 | a | g | CTTTGAAATCTTNTAGTTCTGCTGC | SEQ ID NO:90 |
| 90 | 4 | t | c | TTCCTCACTGTANTGCTTATTCTCT | SEQ ID NO:91 |
| 91 | 4 | t | c | GAGCCTGGCATANGAAACAATTTCC | SEQ ID NO:92 |
| 92 | 4 | g | a | GAACACAATAACNAAACAGATGATG | SEQ ID NO:93 |
| 93 | 4 | t | c | CTGGGTTGCTTCNTGTAAACCTGCA | SEQ ID NO:94 |
| 94 | 4 | g | a | CTAAAAGTAAATNTCGGTATCAGTG | SEQ ID NO:95 |
| 95 | 4 | g | a | TAGATAGCATGCNGCTTCAAGAAGA | SEQ ID NO:96 |
| 96 | 4 | c | t | CAGCGATGTTCANTGGCGGCTTATT | SEQ ID NO:97 |
| 97 | 4 | g | a | CACTAATCAAGTNCACTAGCCCTCC | SEQ ID NO:98 |
| 98 | 4 | g | a | CTTTTTACCACTNAACTCTGGAATG | SEQ ID NO:99 |
| 99 | 4 | a | g | TTCAAATCATCCNCAGACTTGTTCA | SEQ ID NO:100 |
| 100 | 4 | a | g | TGTTTTCTGGACNCATAGCTCATGT | SEQ ID NO:101 |
| 101 | 4 | t | a | CTGGGCAAATCANCCATTAACACTC | SEQ ID NO:102 |
| 102 | 4 | t | a | TTTTGGAGGACCNCAATCATGGTTC | SEQ ID NO:103 |
| 103 | 5 | c | t | ATTACCTCCTTANGCAAATGACCAC | SEQ ID NO:104 |
| 104 | 5 | g | a | GAATCGTGGGGCNTTTTGGCAGCCT | SEQ ID NO:105 |
| 105 | 5 | t | c | ACACTACAGTAANACCTCTAGCCCA | SEQ ID NO:106 |
| 106 | 5 | g | t | AAACATGATTATNCTCCTGCATTGA | SEQ ID NO:107 |
| 107 | 5 | c | a | GGAACTGGAAAGNAACTTCCATCAG | SEQ ID NO:108 |
| 108 | 5 | c | t | TGTCAGGCACTTNAGGGCATTGACC | SEQ ID NO:109 |
| 109 | 5 | g | a | GGAGCCATGAGANTTATTGCGGCCC | SEQ ID NO:110 |
| 110 | 5 | c | t | TGTGCTTTCTGANGCCTACCTCCAA | SEQ ID NO:111 |
| 111 | 5 | c | t | AAGTGGAGGGCGNTCATTCCATCCT | SEQ ID NO:112 |
| 112 | 5 | g | a | GAAATCATGTCCNCCCTTTTCCAGT | SEQ ID NO:113 |
| 113 | 5 | c | t | TACCTATTCGCCNTCCATGAAACAG | SEQ ID NO:114 |
| 114 | 5 | t | c | TGAGATTTCCTANGATGGAAGTGTG | SEQ ID NO:115 |
| 115 | 5 | t | c | CTGTTTCCTTTCNGGTTGGTTCGTT | SEQ ID NO:116 |
| 116 | 5 | t | c | CGCAGTACAAGGNTTCCCTAGTAGT | SEQ ID NO:117 |
| 117 | 5 | t | c | ACAGTATTTGGANGGCTGACTAAAA | SEQ ID NO:118 |
| 118 | 5 | g | a | CTAAAAGTGGACNAGAGCCTTAAAA | SEQ ID NO:119 |

TABLE 1-continued

| SNP | CHROMOSOME | REF_ BASE | ALT_ BASE | 25MER | Sequence Indentifier |
|---|---|---|---|---|---|
| 119 | 5 | c | g | AAAGCCTCCACGNGACAACAGTTTC | SEQ ID NO:120 |
| 120 | 5 | a | g | GAGACCTCAAAGNTTCACAACATGA | SEQ ID NO:121 |
| 121 | 5 | t | c | TCACTGCATATANTAACATAAAAAC | SEQ ID NO:122 |
| 122 | 5 | a | g | TATTATTATCCCNTTGTAAATGTTT | SEQ ID NO:123 |
| 123 | 5 | a | g | ATATTGTCACTGNTGCCCTTGATTG | SEQ ID NO:124 |
| 124 | 5 | c | t | GCACCTAACCATNTGCTGACGTGGC | SEQ ID NO:125 |
| 125 | 6 | c | t | TTACAGGTTTCANTTTTTTATCGTC | SEQ ID NO:126 |
| 126 | 6 | t | a | AAAAGTTTAGGANCATAGTAAGGTT | SEQ ID NO:127 |
| 127 | 6 | t | g | AAACTCTATGCTNTGGCCTTTCATA | SEQ ID NO:128 |
| 128 | 6 | c | t | CATTATGAATTCNTTCGTCACTGAT | SEQ ID NO:129 |
| 129 | 6 | g | t | AAGGCAGAGCACNTTTCTGTGGTTC | SEQ ID NO:130 |
| 130 | 6 | c | t | TTTAGAAATAGCNGGTGATTACAGA | SEQ ID NO:131 |
| 131 | 6 | g | c | TACAGAACCTTANACAGACTACGTA | SEQ ID NO:132 |
| 132 | 6 | g | c | CAGAGCTTATTCNTTCTACCTTGTT | SEQ ID NO:133 |
| 133 | 6 | a | g | GCATGTCTCACANCATTACGAATGG | SEQ ID NO:134 |
| 134 | 6 | t | c | TGCATAGTAATCNTTCATTCAGCAC | SEQ ID NO:135 |
| 135 | 6 | c | t | TAGCTACAGTTANCGATTCCGCTTA | SEQ ID NO:136 |
| 136 | 6 | c | t | AGTATTTGTCAANTAATGCTGTTAA | SEQ ID NO:137 |
| 137 | 6 | g | t | AAGGCTTTCCTGNAAAAGTAGCTGT | SEQ ID NO:138 |
| 138 | 6 | a | c | TAGCAGCATTCANGGGACTCAGGTG | SEQ ID NO:139 |
| 139 | 6 | t | c | GCAATAGCTAATNGAGTTCCTGATT | SEQ ID NO:140 |
| 140 | 6 | t | a | TACTTTGATTAANGGCTGATGATAT | SEQ ID NO:141 |
| 141 | 6 | g | c | TTAAAATTTGTCNGTGCCAATTTAG | SEQ ID NO:142 |
| 142 | 6 | t | g | TACCTGTGTAAANAAATTGATAACA | SEQ ID NO:143 |
| 143 | 6 | g | a | GTCCAATTAGCANTAAGTGCCATGC | SEQ ID NO:144 |
| 144 | 6 | t | g | CTTTTGTTCATTNGATAATCGGGTG | SEQ ID NO:145 |
| 145 | 6 | a | g | GAATGTCTGCTCNGTTACAACGTGA | SEQ ID NO:146 |
| 146 | 7 | t | c | GCATGTATTGTCNATCCAAAAACTT | SEQ ID NO:147 |
| 147 | 7 | a | g | AATTCAGACCACNCTTAGGGAATCA | SEQ ID NO:148 |
| 148 | 7 | t | c | GTCCACAAAGGTNTGGAATATAAAA | SEQ ID NO:149 |
| 149 | 7 | g | t | TTGTGATATTCCNCCAAAGTAAACA | SEQ ID NO:150 |
| 150 | 7 | g | t | TCTGTACCTCATNTACTTGTAGTCT | SEQ ID NO:151 |
| 151 | 7 | t | c | ACTCAGGTGCATNCAGAGCCGAAGG | SEQ ID NO:152 |
| 152 | 7 | c | t | AGTCAATGCTTANTTAAGCTTATTC | SEQ ID NO:153 |
| 153 | 7 | g | a | ACATGGTAGCAGNAAATGAGAGCGT | SEQ ID NO:154 |
| 154 | 7 | t | c | GTTATAAAGCCTNTCCAGGTGCAGA | SEQ ID NO:155 |
| 155 | 7 | c | t | TCAAGTGCCTGCNACAAGTAAATAG | SEQ ID NO:156 |
| 156 | 7 | g | a | CATGTATAAGCCNAAAGCTAAAACG | SEQ ID NO:157 |

TABLE 1-continued

| SNP | CHROMOSOME | REF_ BASE | ALT_ BASE | 25MER | Sequence Indentifier |
|---|---|---|---|---|---|
| 157 | 7 | c | t | CACTCGAGCATGNGGCATTATTTAA | SEQ ID NO:158 |
| 158 | 7 | c | t | ATCAGTCATTTCNGGCTCTTTATGT | SEQ ID NO:159 |
| 159 | 7 | t | c | AGCCAAACCATANCTAGTTTCCAAA | SEQ ID NO:160 |
| 160 | 7 | c | t | ATGTGATACTTANGAATTCCACCAG | SEQ ID NO:161 |
| 161 | 7 | g | a | GTACCTCTAGACNTCCATACAGCTT | SEQ ID NO:162 |
| 162 | 7 | g | a | ACAGCTGAGTGANAACAAAATGGAC | SEQ ID NO:163 |
| 163 | 7 | g | a | TACAGTACAGACNTTGATGAGACCA | SEQ ID NO:164 |
| 164 | 8 | g | c | AGTCTTATCTTTNGGACAAATGGAA | SEQ ID NO:165 |
| 165 | 8 | g | a | TCCAAGCCTCCCNGAATGAAACTTT | SEQ ID NO:166 |
| 166 | 8 | g | c | CCACTTCTAATANCTTTCACAAGAC | SEQ ID NO:167 |
| 167 | 8 | t | a | CGTAAACTGAGCNGACCTGTACCCT | SEQ ID NO:168 |
| 168 | 8 | t | c | CTGTGTTAAACTNCCAGATGGCAGT | SEQ ID NO:169 |
| 169 | 8 | g | c | CAGCTGGAAACANGTCTGGGCTCTT | SEQ ID NO:170 |
| 170 | 8 | g | a | GTTAACCAGCCTNAATGCAAAAAGT | SEQ ID NO:171 |
| 171 | 8 | c | t | AACAGCCAGAGTNCCTGTAAGAGCA | SEQ ID NO:172 |
| 172 | 8 | c | t | GGCATACATCTTNCTTAACCTACAT | SEQ ID NO:173 |
| 173 | 8 | c | g | GGTCCAAAAGTCNTGCTAGGTATCT | SEQ ID NO:174 |
| 174 | 8 | g | a | GGCAAGACCTCANAATAACTTAAAG | SEQ ID NO:175 |
| 175 | 8 | a | t | ATGCGTAGGTTANGGTCCTAGTTCA | SEQ ID NO:176 |
| 176 | 8 | c | a | GTGCTACTTTGANTGTGAAAATACA | SEQ ID NO:177 |
| 177 | 8 | t | c | CTCAGGAAAGAANTGCCACTTCGAA | SEQ ID NO:178 |
| 178 | 8 | c | t | ATTTGATGTGACNGATAGCTCCAGA | SEQ ID NO:179 |
| 179 | 8 | c | t | CAGAGCCAAAAANGTTGCTCTTCCA | SEQ ID NO:180 |
| 180 | 8 | t | c | ATGCTACTGATANGTAATCACAATG | SEQ ID NO:181 |
| 181 | 8 | g | a | ACCCTTTCTACTNTACTATCACAGC | SEQ ID NO:182 |
| 182 | 9 | g | a | CAGTGTTCTTTGNGGTTCCACTCTT | SEQ ID NO:183 |
| 183 | 9 | t | c | CTAGTGCTTTCANGATGCCCTTAGT | SEQ ID NO:184 |
| 184 | 9 | c | t | GTTACCCTTACANGTGGCTGTTTGC | SEQ ID NO:185 |
| 185 | 9 | t | a | TTCTAACTCTCANTTAAGTGAGGCA | SEQ ID NO:186 |
| 186 | 9 | a | g | CTCACATTACCCNACTTTGGGCCCT | SEQ ID NO:187 |
| 187 | 9 | t | c | GCCAATGTTTAGNGGAGATATTTCT | SEQ ID NO:188 |
| 188 | 9 | c | t | TGTTCAAGCCATNGATATTAGGTTG | SEQ ID NO:189 |
| 189 | 9 | t | c | GTGTGATGCTCTNTTTTGACCCACA | SEQ ID NO:190 |
| 190 | 9 | t | c | CTTTTCTAATACNGCAATATTTCAA | SEQ ID NO:191 |
| 191 | 9 | g | a | TGAAACTTAGGCNGAATAGTAAGTA | SEQ ID NO:192 |
| 192 | 9 | a | g | TATCATGGGACCNTCCTATAAGGTT | SEQ ID NO:193 |
| 193 | 9 | a | g | TGGAGAGAGGCCNTTTCCTAATCAG | SEQ ID NO:194 |
| 194 | 10 | c | g | CCTGAATGTAATNAATATGTGACAG | SEQ ID NO:195 |

TABLE 1-continued

| SNP | CHROMOSOME | REF_ BASE | ALT_ BASE | 25MER | Sequence Indentifier |
|---|---|---|---|---|---|
| 195 | 10 | c | t | GCATTGGCCTGANGGATAGGCTGCT | SEQ ID NO:196 |
| 196 | 10 | c | a | GTAATCTAGCCANAACAATGGTTGC | SEQ ID NO:197 |
| 197 | 10 | c | t | GTTTGTAAATTTNGTGGATTGAAAG | SEQ ID NO:198 |
| 198 | 10 | c | a | TAAAGGAAAATANTTGAAGTGTTGG | SEQ ID NO:199 |
| 199 | 10 | g | a | CCCAGGAATTTCNAAAGGGAGCACA | SEQ ID NO:200 |
| 200 | 10 | c | g | GGAGTAGAGAAANACAACCTCAATA | SEQ ID NO:201 |
| 201 | 10 | g | a | TAAAAGGCAGTANGAAGGCAGTCCA | SEQ ID NO:202 |
| 202 | 10 | c | a | TTCTGCTGGAAANTTAGGGTGATCA | SEQ ID NO:203 |
| 203 | 10 | g | t | TTTCCCCTGTCANTTTAGCAATCAA | SEQ ID NO:204 |
| 204 | 10 | c | t | TCCTATATGGTGNCCCAAATTCTTA | SEQ ID NO:205 |
| 205 | 10 | c | a | GCCTCCTTTCAANCCTGGTGAGAAG | SEQ ID NO:206 |
| 206 | 10 | a | g | GAAATGTTCCCANGTCCAGCCATGA | SEQ ID NO:207 |
| 207 | 10 | t | a | TTTTAGCGAGGGNTCATTCGTTCAT | SEQ ID NO:208 |
| 208 | 10 | c | t | ATCATAAAAAATNGCCACTCGAGAA | SEQ ID NO:209 |
| 209 | 10 | t | a | TGAAAGCAACCANGGGTCTCTCATC | SEQ ID NO:210 |
| 210 | 11 | a | g | ATTTTGGTAAACNGGACCAGCATTT | SEQ ID NO:211 |
| 211 | 11 | t | g | TCCAATTCATGANGAAAGCCTAAGT | SEQ ID NO:212 |
| 212 | 11 | t | c | GAGCTTTTCCCANGTATGATCTGAC | SEQ ID NO:213 |
| 213 | 11 | g | c | CTAGATCTCTTANCAGTTTAATCCT | SEQ ID NO:214 |
| 214 | 11 | c | t | CAAACTTTGACTNTTGGTACTAAGA | SEQ ID NO:215 |
| 215 | 11 | t | c | CATCATTGGACANCATGAAATATGT | SEQ ID NO:216 |
| 216 | 11 | t | c | ATGAGGAAAATTNGGTACATTCATT | SEQ ID NO:217 |
| 217 | 11 | g | c | AAGTCATTCACANACACAAGTGATT | SEQ ID NO:218 |
| 218 | 11 | t | c | TGACTAAAAAGANTGAGCGTTTGTG | SEQ ID NO:219 |
| 219 | 11 | t | c | ACCTAATATCTANGAAGCCAATTGT | SEQ ID NO:220 |
| 220 | 11 | a | g | TCAGGGATCATANCACTGACAAAAG | SEQ ID NO:221 |
| 221 | 11 | g | a | ACTAAGATGCTGNGAAGACTGCAGG | SEQ ID NO:222 |
| 222 | 11 | a | g | TTGCACGGGAGCNGTTACAACATTT | SEQ ID NO:223 |
| 223 | 11 | c | t | GCATATCAGAAANGTATGACCACAA | SEQ ID NO:224 |
| 224 | 11 | t | c | TGAAACCAAGTTNGTACTCTTGGCT | SEQ ID NO:225 |
| 225 | 12 | t | c | ATTTAATTTGTANTCTTTCGGAAAT | SEQ ID NO:226 |
| 226 | 12 | c | t | AAATACTGCTTANGTAACTTAAGAG | SEQ ID NO:227 |
| 227 | 12 | a | g | AAAGTCTCTTTCNTATTAGCTAAAC | SEQ ID NO:228 |
| 228 | 12 | g | a | GGCCTAAAACCANCCACTTTATATG | SEQ ID NO:229 |
| 229 | 12 | g | a | TGGCTTCCAAGANTCCCCTGGTCAG | SEQ ID NO:230 |
| 230 | 12 | c | g | TTTTCATTGATANAAGGGTGAGCCA | SEQ ID NO:231 |
| 231 | 12 | t | c | AAAGCAGCAAGTNTGGCCATCTAGA | SEQ ID NO:232 |
| 232 | 12 | c | t | ATTCTGCAGGGANCATGGCCAGTTT | SEQ ID NO:233 |

TABLE 1-continued

| SNP | CHROMOSOME | REF_ BASE | ALT_ BASE | 25MER | Sequence Indentifier |
|---|---|---|---|---|---|
| 233 | 12 | t | c | AGATAAACCTTTNACCACGTCTAGA | SEQ ID NO:234 |
| 234 | 12 | c | t | CAAACAGCTTTANGAAAAGTTTTAA | SEQ ID NO:235 |
| 235 | 12 | c | t | GTCAGGCAATTANGAGTACTAGGAG | SEQ ID NO:236 |
| 236 | 12 | a | g | TAATGCTATTTCNTACTATACAACT | SEQ ID NO:237 |
| 237 | 12 | a | g | GATAACCAAATCNTTTTTCGGATTT | SEQ ID NO:238 |
| 238 | 12 | g | a | AAACTTAACTGCNTTCTCAAATAGT | SEQ ID NO:239 |
| 239 | 12 | a | g | GATTTGATCCTTNTAAATTCCATAG | SEQ ID NO:240 |
| 240 | 12 | g | a | TTGCCTTTGGGANGTTCTTTGAGTT | SEQ ID NO:241 |
| 241 | 12 | t | c | TATCCTCAAATTNGGTCACTCAGGT | SEQ ID NO:242 |
| 242 | 13 | g | c | AGCACTTTGTTTNAATGAAACTATA | SEQ ID NO:243 |
| 243 | 13 | a | c | TTCTTGTGTCTCNACATTTTGTATG | SEQ ID NO:244 |
| 244 | 13 | c | t | TATTGGTTCAGANACTATTCGAAAT | SEQ ID NO:245 |
| 245 | 13 | a | g | CAATTGCAGAGANGTTTTCAAATGA | SEQ ID NO:246 |
| 246 | 13 | t | g | TAGATGTGACTGNTTCATTTAGCCA | SEQ ID NO:247 |
| 247 | 13 | t | c | TGATTCCACCATNATCTATAGCTCC | SEQ ID NO:248 |
| 248 | 13 | t | c | TGGGATGTATACNGTGAGTCACTAA | SEQ ID NO:249 |
| 249 | 13 | g | t | GAGTCTACCATTNTATTGGGTACAT | SEQ ID NO:250 |
| 250 | 13 | g | a | AACTTCAGAATANTTCAATTACCCT | SEQ ID NO:251 |
| 251 | 13 | g | t | AAGTCTTTTCCTNTTGAATACCATC | SEQ ID NO:252 |
| 252 | 14 | a | g | ACATTATGGTATNAACTTTGGCTGC | SEQ ID NO:253 |
| 253 | 14 | t | c | ATGGCTTAATCANAAGGAACTACAT | SEQ ID NO:254 |
| 254 | 14 | a | t | TCCCTACCTGAANCAACCCAGTGCA | SEQ ID NO:255 |
| 255 | 14 | g | t | AACTGCTACATTNGGAGCTTTCTGA | SEQ ID NO:256 |
| 256 | 14 | a | g | GGTTTGACTGCCNACGATGCTAAGA | SEQ ID NO:257 |
| 257 | 14 | c | t | TACAAAGTAGTGNAGCTGTACATCA | SEQ ID NO:258 |
| 258 | 14 | c | t | TCTCAGGAGAAGNGGCCCTTCTGAT | SEQ ID NO:259 |
| 259 | 14 | c | t | ATTGCAAACTTANGATATTCACAAA | SEQ ID NO:260 |
| 260 | 14 | g | a | GTGCTTGCCTCCNCTCTATCGGGCG | SEQ ID NO:261 |
| 261 | 15 | t | c | GATGCACGATACNAGAAATAAGCAT | SEQ ID NO:262 |
| 262 | 15 | g | a | ATCGCCTTGATANAAATATGATATG | SEQ ID NO:263 |
| 263 | 15 | c | t | CTACTGCTTCATNGCCCTCTAGTAC | SEQ ID NO:264 |
| 264 | 15 | t | g | TTGTTGTGCGTGNCTTGGATAGCAA | SEQ ID NO:265 |
| 265 | 15 | g | a | ACCTGTGCGTGCNAAACCCATGGCA | SEQ ID NO:266 |
| 266 | 15 | g | a | TGCGGGACCTGCNAAAATGTATCCC | SEQ ID NO:267 |
| 267 | 15 | g | a | GTGTTTTTAATCNTAGCTCTTTACT | SEQ ID NO:268 |
| 268 | 16 | a | g | ACAGTAACAATCNATCATTATGAGC | SEQ ID NO:269 |
| 269 | 16 | g | a | TTTTTACTTCCCNTCAAATCACAAG | SEQ ID NO:270 |
| 270 | 16 | t | g | ACCATTGAGAGGNTCCCCTTAGCCA | SEQ ID NO:271 |

TABLE 1-continued

| SNP | CHROMOSOME | REF_ BASE | ALT_ BASE | 25MER | Sequence Indentifier |
|---|---|---|---|---|---|
| 271 | 16 | c | t | TGTTATTTTATCNGATTGAATTGTG | SEQ ID NO:272 |
| 272 | 16 | g | a | ATTTCGTATTTTNAATGCCCCACAA | SEQ ID NO:273 |
| 273 | 16 | a | g | CCATGAAAGATGNCTCCAGAAACTT | SEQ ID NO:274 |
| 274 | 16 | t | c | TACTGACCGTCCNGACGCTTTCAGT | SEQ ID NO:275 |
| 275 | 16 | g | c | ACTTTGTCACATNAAACAAGATGAG | SEQ ID NO:276 |
| 276 | 16 | c | t | CTTTGAAAACTGNGGGATGAGTTAG | SEQ ID NO:277 |
| 277 | 17 | c | t | TCTGACTCAATCNGCCTGTCTTTAG | SEQ ID NO:278 |
| 278 | 17 | t | c | CAGGAGACAGCTNGGGGTCACGGCG | SEQ ID NO:279 |
| 279 | 17 | g | c | CTGTCTCTACCANGTAACACATGAC | SEQ ID NO:280 |
| 280 | 17 | g | a | CTCGGTCTTGACNGTCTGAATTACT | SEQ ID NO:281 |
| 281 | 17 | g | a | TCCAGACAAAGGNATCAGTGCAAGC | SEQ ID NO:282 |
| 282 | 17 | t | c | TCTCCTATTTGTNCCATGGCAGTTA | SEQ ID NO:283 |
| 283 | 17 | c | a | GTTACTGACGGGNTTTAGCCATTAC | SEQ ID NO:284 |
| 284 | 17 | a | g | TTACTTTTCACANTCTCTCTAACAT | SEQ ID NO:285 |
| 285 | 17 | a | g | GGTTCTGAGAGCNCCACAAGGAAGA | SEQ ID NO:286 |
| 286 | 18 | c | g | TATCTTAGCCTANTAGAATGGAATC | SEQ ID NO:287 |
| 287 | 18 | a | g | TTGAGGGTGTGANTTTTCTGTATCC | SEQ ID NO:288 |
| 288 | 18 | g | c | TACTTTGTCCCTNTCATAGAACCTG | SEQ ID NO:289 |
| 289 | 18 | t | a | GTGCATTCTTCANACTGATTTGGGA | SEQ ID NO:290 |
| 290 | 18 | g | a | AGCAGGCTAAAGNTTTCACTGAAGT | SEQ ID NO:291 |
| 291 | 18 | a | g | ATTATCATTTGCNTAAGCCTCTCAT | SEQ ID NO:292 |
| 292 | 18 | g | a | CATACACTTCCANATCTTCTGTAGC | SEQ ID NO:293 |
| 293 | 19 | c | t | AATGATAAAAGANGACCCATGCCTT | SEQ ID NO:294 |
| 294 | 19 | a | g | CAATCTAATGCCNCAAGAAAAAATA | SEQ ID NO:295 |
| 295 | 19 | t | c | TGTTATTCCAACNCTGAACACATCA | SEQ ID NO:296 |
| 296 | 19 | a | g | TGACTGAGAGTANTGGACACAGTTT | SEQ ID NO:297 |
| 297 | 19 | g | a | GACACGCTAGACNAAGGGCGTCCAT | SEQ ID NO:298 |
| 298 | 19 | a | c | TGGGAATGTAATNGGCAGTTTAAGA | SEQ ID NO:299 |
| 299 | 19 | t | c | GACTTGAAAAAANCCAGACTTTTGA | SEQ ID NO:300 |
| 300 | 19 | c | t | AGAGGAACAAAANGGTAAGTAATTA | SEQ ID NO:301 |
| 301 | 20 | t | c | CCAAAACTCTTANAAATTCTATGGT | SEQ ID NO:302 |
| 302 | 20 | a | c | ACGAAAATCATANGACTCTACGGAA | SEQ ID NO:303 |
| 303 | 20 | a | g | CAAATTTCCACTNTCCCGAGAAGGT | SEQ ID NO:304 |
| 304 | 20 | c | g | AAAGTCATTGTTNTCAAATGGGATG | SEQ ID NO:305 |
| 305 | 20 | a | g | TATCTTTAAGCANTTTAGCAAGTAG | SEQ ID NO:306 |
| 306 | 21 | a | g | GATGATTACAGTNGTCGTAGTTCCC | SEQ ID NO:307 |
| 307 | 21 | c | t | AGTAAATAGCTCNTTTCTTTGTAGA | SEQ ID NO:308 |
| 308 | 21 | g | a | AGTCCTTGAAGANTGATCATAAAAA | SEQ ID NO:309 |

TABLE 1-continued

| SNP | CHROMOSOME | REF_ BASE | ALT_ BASE | 25MER | Sequence Indentifier |
|---|---|---|---|---|---|
| 309 | 22 | g | t | GCGGACCTGAGTNACCTCATGGAAC | SEQ ID NO:310 |
| 310 | 22 | g | a | ATCAGATGACCANGAATTGAGAGAC | SEQ ID NO:311 |
| 311 | 22 | a | g | CTACAGAGGTACNTGCATAGGTCCA | SEQ ID NO:312 |
| 312 | 22 | c | t | TTTTTCTATAGANGGCCAGCACTGG | SEQ ID NO:313 |

Figure 3B:
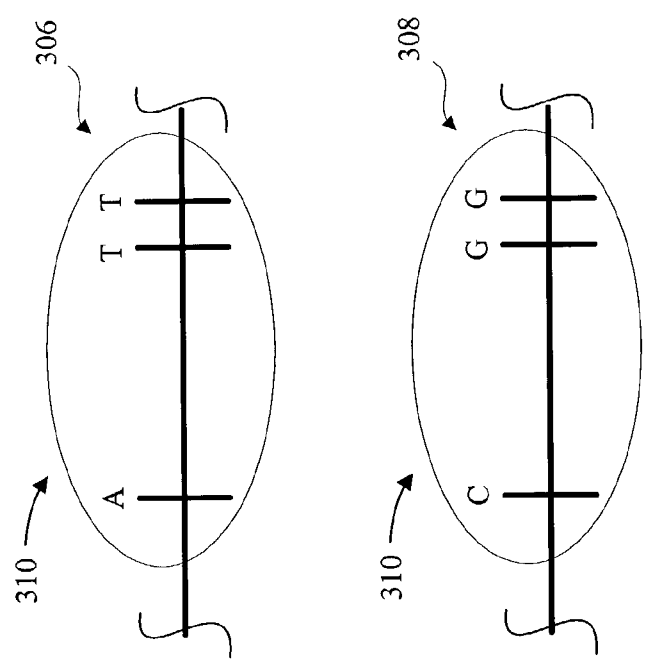
FIG. 3B is a diagrammatic representation of a single nucleotide polymorphism.

As indicated above, the genetic markers can include SNPs, microsatellites, or the like. A SNP is a single nitrogenous base position in the DNA of organisms that is variable, and typically arises due to substitution of one nucleotide for another at the polymorphic site. To illustrate this concept, FIG. 3B shows genomic sequences 306 and 308 corresponding to relatively short regions of two chromosomes, each having the same three SNP positions. Each SNP position is bi-allelic, generally exhibiting one of two alleles. In this case, the left-most depicted SNP has an A allele in sequence 306 and a C allele in sequence 308. Additionally, the two right-most SNPs have T alleles in sequence 307 and G alleles in sequence 308. As shown in FIG. 3B, the region circled at location 310 corresponds to a haplotype block, which is a contiguous region of sequence that exhibits a reduced set of observed allele combinations in comparison to all possible allele combinations. Haplotype blocks reflect descent from a single ancient ancestral chromosome and result in reduced genetic variability. As such, SNPs within a haplotype block tend to be inherited together. Thus, the only SNP allele combinations that would commonly occur for haplotype block 310 are A-T-T and C-G-G.

Turning again to FIG. 2, at 200, a DNA sample is obtained from the individual according to any known method. For example, a sample of saliva or blood can be collected from the individual.

Next, at 202, a polymerase chain reaction ("PCR") or other amplification technique is used to amplify the DNA sample at various genomic regions. Each of these various regions preferably contains one of the multiple markers chosen to identify differences in ethnicity.

In one example, PCR is used to amplify the DNA sample at 312 regions containing the 312 above-mentioned genetic markers. For each marker, two primers are provided as well as the nucleotide monomers, polymerase and other components commonly employed in PCR.

Figure 3A:
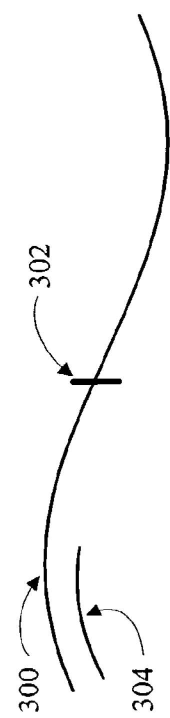
FIG. 3A is a diagrammatic representation of an amplicon.

As is well-known, the combined mixture is heated to a "melting" temperature (e.g., ninety-five degrees Celsius) to denature the DNA strands in the sample. After denaturing the DNA strands, the mixture can be cooled to an "annealing" temperature (e.g., 37 degrees Celsius) to allow the primers to hybridize with complementary portions of the single-stranded DNA in solution. FIG. 3A shows a nucleic acid sequence 300 to be amplified, that includes a marker 302. As shown, a primer 304 has hybridized with nucleic acid sequence 300. Next, the mixture is heated to 72 degrees Celsius to allow the polymerase to "extend" the complementary region beyond the end of primer 304. A different primer works from the opposite end of a nucleic acid sequence complementary to nucleic acid sequence 300. The cycle of denaturing and hybridizing can be repeated to produce an exponentially increasing number of amplified DNA strands. A more detailed description of the PCR can be found in various textbooks, such as Sambrook, et al., *Molecular Cloning: A Laboratory Manual* (Cold Spring Harbor Laboratory, New York) (2001); Innis, et al., *PCR Applications: Protocols for Functional Genomics* (Academic Press) (1999); and Newton, C. R. (ed.), *PCR* (John Wiley & Sons Ltd.) (1995), which are incorporated herein by reference in their entirety for all purposes. Further descriptions of PCR methods may be found in U.S. patent application Ser. No. 10/042,406, filed Jan. 9, 2002; U.S. patent application Ser. No. 10/042,492, filed Jan. 9, 2002; U.S. patent application Ser. No. 10/236,480, filed Sep. 5, 2002; U.S. patent application Ser. No. 10/174,101, filed Jun. 17, 2002; and U.S. patent application Ser. No. 10/341,832, filed Jan. 14, 2003, all of which are incorporated by reference in their entirety for all purposes.

As described above, PCR is performed for each of the various genetic markers (e.g., the 312 SNPs identified herein). In the simplest approach, PCR is performed in separate a vessel for each of the markers. Alternatively, and more efficiently, PCR can be multiplexed, such that several markers are amplified simultaneously in a single reaction vessel. In certain embodiments, at least about 5 to 100 markers are amplified in a single PCR reaction; in other embodiments, at least about 10–80 markers are amplified in a single PCR reaction; in still other embodiments, at least about 20–60 markers are amplified in a single PCR reaction. This is accomplished by exposing a single sample to multiple primer pairs, one pair for each region of DNA to amplified. Multiplexing can greatly enhance the sequencing speed for the various sequences, but multiplexing should be performed with care to avoid interference between the various sequences during the PCR. Accordingly, the markers and primers chosen for multiplexing can be selected to reduce the chance of interference between the sequences to be amplified simultaneously.

After amplifying the DNA at each of the genetic markers, the amplified DNA is pooled together into one sample per individual at step 204. At 206, this pooled DNA sample is tagged with a fluorescent reporter or other signal group by standard biochemical methods and applied to a DNA array. DNA arrays are typically made from DNA probe wafers that include high-density arrays of DNA probes placed on a glass wafer. These wafers are typically made using processes adapted from the semiconductor manufacturing industry. Such wafers are diced into chips, which are available from, for example, Affymetrix, Inc. of Santa Clara, Calif. In this case, the probes are chosen to identify the presence of the various alleles for each of the genetic markers. A chip composed of such probes is sometimes referred to as a "stratification chip."

After the pooled DNA sample is applied to the DNA array, the sample and chip can be incubated. During incubation, segments of the pooled DNA sample can hybridize with complementary sequences of probes on the DNA chip. By evaluating which probes hybridize to segments of the pooled DNA sample, it is possible to determine what marker alleles are present in the DNA sample.

Thus, at 208, once segments of the DNA sample have hybridized with complementary sequences on the wafer, the DNA sample can be genotyped. More particularly, after segments of the DNA sample have hybridized with complementary probes on the wafer, any unbound DNA strands can be washed from the wafer. The wafer is then scanned to detect which of the probes on the DNA wafer have hybridized with the DNA sample. Typically, the DNA sequences are tagged with a fluorophore so that they will fluoresce under certain excitation conditions and, hence, be detectable to a laser scanning device. There are many different fluorophores available for labeling nucleic acids that are well known in the art, including, but not limited to, fluorescein and rhodamine. Because the identity and position of each probe on the DNA chip is known, the allelic values for each of the markers can be obtained for the individual, based on which of the probes hybridized with the DNA sample.

Although the present example describes using genomic DNA samples with a particular set of genetic markers, it should be recognized that the techniques of the present invention can be also used to characterize any number and type of bi-allelic or multi-allelic genetic markers in nucleic acid sequences derived from any organism, such as an animal, human, insect, or bacterium. In addition, although the present example describes genotyping by using DNA arrays, it should be recognized that other methods can be used to genotype individuals in the case and control groups. Generally, suitable techniques may utilize, for example, enzymatic, electrophoretic, chromatographic, or physical methods for discriminating allelic variants. Detection methods for genotyping may involve, for example, fluorescence detection, fluorescence resonance energy transfer, fluorescence polarization, electrochemical detection, mass spectrometry, or atomic force microscopy.

With reference to FIG. 4, an exemplary chart showing allele counts in case and control groups is shown for each of the 312 SNPs discussed above with regard to FIG. 2. This chart can be constructed from the results of genotyping each member of the case and control groups at 102 of FIG. 1. As shown, column 400 uniquely identifies each of the 312 SNPs. Column 402 lists the number of chromosomes from individuals in the case group having allele X for each of the respective markers. Column 404 lists the number of chromosomes from individuals in the case group having allele Y for each of the respective markers. Similarly column 406 lists the number of chromosomes in the control group having allele X for each of the respective markers and column 408 lists the number of chromosomes in the control group having allele Y for each of the respective markers. As shown, each of the case and control groups includes 100 individuals. The DNA samples taken from each of the 100 individuals include diploid cells having two sets of chromosomes. Each individual was genotyped for these two sets of chromosomes, thereby producing a total of two alleles per individual for each marker. Thus, for the 100 individuals in each of the case and control groups, a total of 200 alleles are included in the chart for each marker. If haploid cells had been used, only one set of chromosomes would be available for genotyping, and a total of 100 alleles would be included in the chart for each marker.

From the information in columns 402, 404, 406, and 408, a chi-squared statistic and corresponding p-value can be calculated for each of the 312 SNPs, which indicates the probability of a more extreme outcome if the case group and control group are matched. Higher p-values indicate relatively closely matched allele frequencies in the case and control groups, while lower p-values indicate relatively unmatched allele frequencies. Accordingly, if the p-values are consistently low, there is a strong likelihood that the case and control groups are unmatched.

While a single marker is not sufficient to draw a conclusion about the similarity of the population structures of a case group and a control group, it contributes to such a conclusion. For instance, SNP 1 in the table has very similar frequencies in the two groups and a correspondingly large p-value. On the other hand, SNP 2 has a fairly large difference in allele distribution in the two groups and has a p-value of only 0.02, indicating it is fairly unlikely to see such a large difference by chance. Because a large number of markers are analyzed together, it is not unlikely that a fairly small p-value will occur for one or another marker by chance.

Figure 5:
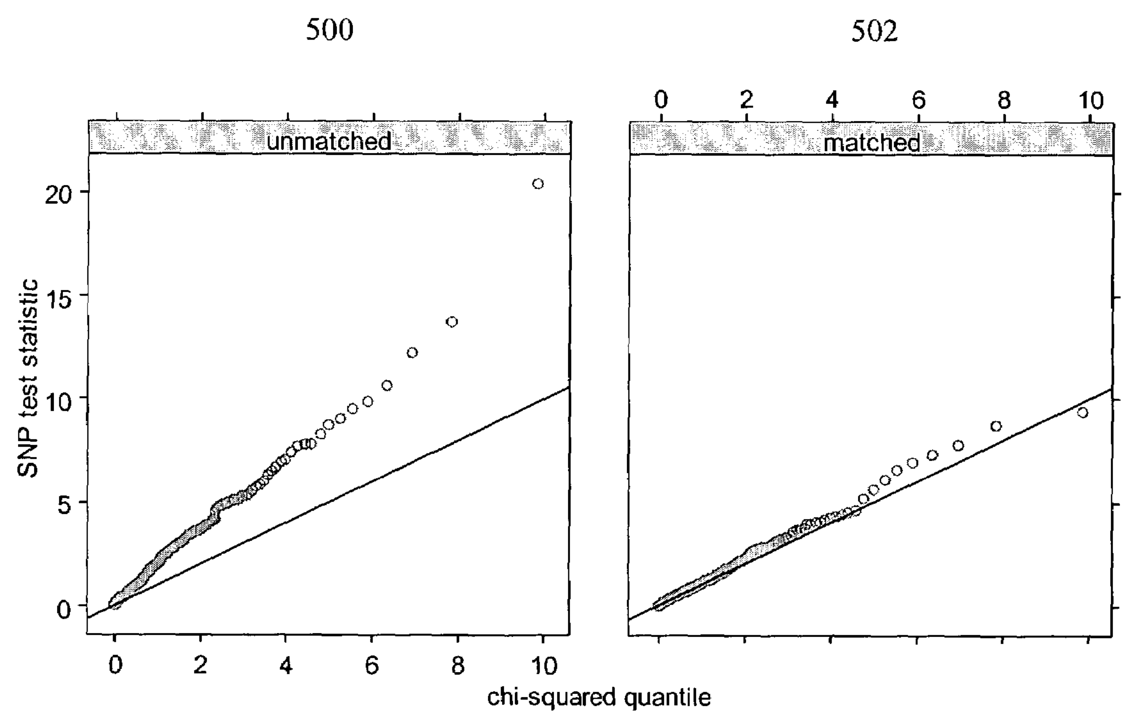
FIG. 5 shows exemplary quantile plots for chi squared statistics from unmatched versus matched case and control groups.

With reference to FIG. 5, shown is an exemplary "Q—Q" plot illustrating observed and expected distributions of chi squared statistics for 312 markers. The positions of the data points along the Y axis represent the observed values ranked in order from smallest to largest. The positions of the points along the horizontal axis represent an equal number of values calculated to conform to the ideal chi squared distribution. If the observed and expected distributions are similar, then the plot should have a slope close to 1. If case and control groups are not well matched, the expectation is that a plot of this type will show a slope greater than 1, i.e., an excess of large chi squared statistics, corresponding to an excess of small p-values. Plot 500 indicates a distribution of chi squared statistics for a study where cases and controls are not well matched; the slope of the data is clearly greater than one. Plot 502 shows typical results for matched case and control groups; the slope of the data is very close to one.

With reference to FIG. 6, an exemplary table showing various probabilities for case and control groups is shown. This is essentially a tabular depiction of the plot presented in FIG. 5. Thus, the table can be constructed from the chart shown in FIG. 4. As shown in column 600, the table includes two rows, one for the expected frequency distribution and the other for the observed frequency distribution. Column 602 includes the number of markers having a p-value less than 0.1, column 604 includes the number of markers having a p-value less than 0.01, and column 608 includes the number of markers having a p-value less than 0.001. As described above, a uniform distribution of p-values (i.e., roughly 50% of markers having p-values less than 0.50, 10% less than 0.10, 1% less than 0.01) indicates that the case and control groups are matched. But an excess of smaller p-values indicates that the case and control groups are not matched. The information contained in this table or in a graph in FIG. 5 can be used to determine whether the difference between the observed and expected frequency distributions is acceptable.

Specific statistical criteria for determining that groups are sufficiently matched will necessarily depend on details of each study design. The methods of the present invention can be used for a broad range of different study designs, each with their own criteria for determining whether or not two groups are well matched. Factors that will influence these criteria include, but are not limited to, the number of individuals in the study, the magnitudes of other sources of experimental error, and the tolerance for false positives. For example, the groups might be sufficiently matched if the expected magnitude of spurious allelic differences due to population structure differences between the groups is small compared to other sources of error in the experiment; or, if the expected increase in false positive rate due to those population structure differences is small compared to the false positive rate expected in the absence of the population structure differences.

As indicated in the discussion of FIG. 1, when the separation of the expected and observed distributions of allelic differences exceeds a threshold, one should adjust the composition of the case and/or control group. See blocks 108 and 114. This may be accomplished by adding or subtracting members from the groups. To do this effectively, one should understand the population structure of the groups. This may be accomplished with stratification analyses.

With reference to FIG. 7A, an exemplary stratification table is shown. Column 700 represents the fraction of a particular ancestry represented in a population. In one example, the population is composed of individuals having some fraction of Native American ethnicity and some fraction of Caucasian ethnicity with column 700 representing the fraction of Native American ancestry for an individual in a case or control group.

The first row of the table shown in FIG. 7A includes individuals that are eighty to one hundred percent Native American ancestry. The second row includes individuals that are sixty to eighty percent Native American ancestry (or twenty to forty percent Caucasian ancestry). The third, fourth, and fifth rows similarly indicate a percentage of Native American ancestry. Column 702 represents the number of individuals in the case group having a particular percentage of Native American ancestry. Similarly, column 704 represents the number of individuals in the control group having a particular percentage of Native American ancestry. For instance, five people in the case group have between eighty to one hundred percent Native American ancestry.

The above stratification table can be constructed using the data obtained from genotyping case and control groups for multiple markers, as described above with regard to operation 102 in FIG. 1. In particular, this data can be input into an algorithm that performs a cluster analysis. The goal of a cluster analysis in accordance with this embodiment is to group individuals from the case group and control group based on similar allele patterns. Generally, a clustering algorithm will attempt to maximize differences between groups, while minimizing differences within groups. Various such algorithms are suitable for use with this invention.

In one embodiment, the genotypes for individuals of the case group or control group is input for analysis by a computer program called "Structure," which is available from the author's web site at pritch.bsd.uchicago.edu. This program is described in Pritchard et al., "Inference of Population Structure Using Multilocus Genotype Data," Genetics (June 2000) vol 155, 945–959, which is incorporated herein by reference for all purposes. The number of desired groupings, as shown in column 700 of FIG. 7A, is input into the program. As shown, column 700 includes five groupings based on the percentage of Native American ancestry.

The "Structure" program analysis estimates the fraction of an individual's genome that seems to come from a certain homogeneous ancestral population. More specifically, the Structure program uses the genotypes (the allele pairs for each marker in each individual) to cluster individuals having similar allele patterns. These clusters are then output as N groups, where N is the number of desired groupings input to the program. As shown in FIG. 7A, the output can be expressed as clusters of people having a particular fraction of a specified ancestry. It should be recognized that this output can be presented in any form, such as a table, chart, or list.

As shown in FIG. 7A of the present embodiment, the distribution of Native American ancestry differs between the case group and control group. Specifically, the case group includes five individuals having eighty to one hundred percent Native American ancestry, whereas the control group includes thirty individuals having the same fraction of Native American ancestry. Based on this comparison, along with the rest of the data in the table, the control group has a greater proportion of Native American ancestry. If the difference between observed and expected frequency distributions for the case and control groups is not within an acceptable range, as determined in accordance with 108 of FIG. 1, then the composition of the case and control groups can be adjusted. Typically, a determination that the case and control groups are unbalanced is made prior to applying a stratification analysis, such as one giving the results depicted in FIG. 7A.

FIG. 7B is an adjusted version of the exemplary stratification table shown in FIG. 7A. As shown, a total of fifty individuals were removed from each of the case and control groups. In particular, from the case group, twenty-five individuals having zero to twenty percent Native American ancestry were removed, and twenty-five individuals having twenty to forty percent Native American ancestry were removed. In addition, from the control group, twenty-five individuals having eighty to one-hundred percent Native American ancestry were removed, and twenty-five individuals having sixty to eighty percent Native American ancestry were removed. After removing these fifty individuals from each of the case and control groups, the frequency distribution of individuals with Native American ancestry in the case and control groups is similar from the perspective of the clustering algorithm, as shown in FIG. 7B. These groups are now matched with regard to Native American ancestry. If the recast groups now produce a relatively small difference between the expected and observed distributions of allele differences, then they can be used in an association study. See operations 114, 108, and 106 of FIG. 1. As discussed above, conducting an association study using these matched groups can increase the chance that any difference in allele frequencies between the groups is causally related to the phenotypic trait of interest, and reduce the chance that this difference is related to population structure differences between the two groups.

Figure 8:
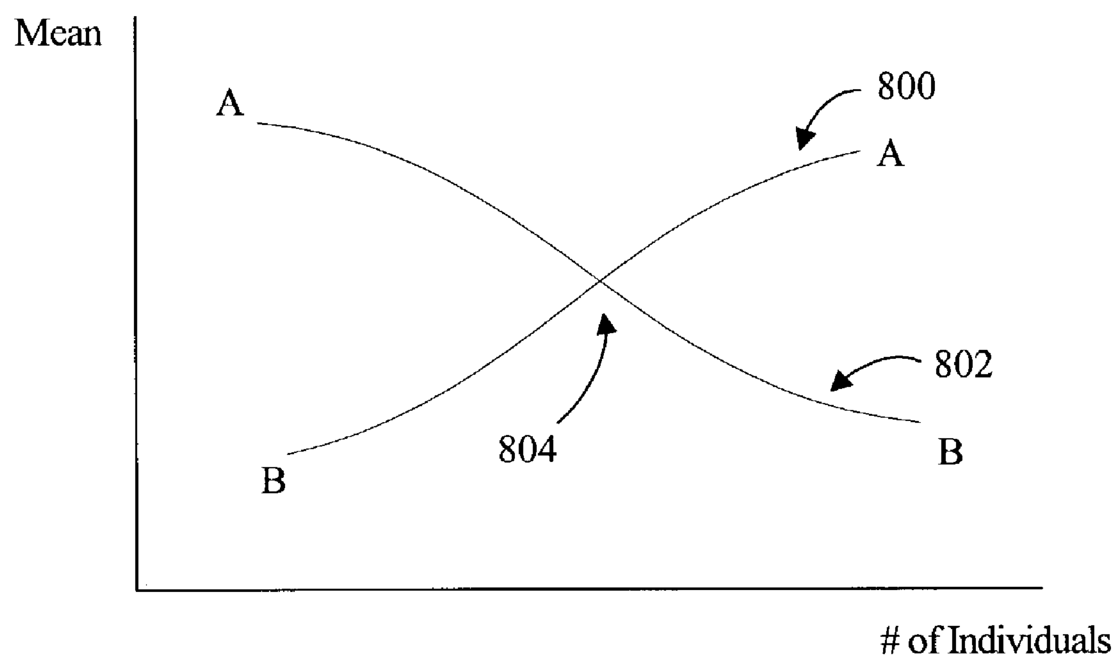
FIG. 8 is an exemplary graph showing mean curves for case and control groups.

The case and control groups can be adjusted according to a variety of methods. The stratified approach depicted in FIG. 7B is only one such method. It can be problematic when there is a limited pool of potential members for the groups. It may eliminate too many individuals, so that the groups no longer represent a statistically significant sampling. One method that addresses this issue continually recomputes the mean frequencies of the case and control groups as it gradually adjusts these groups until they have equivalent mean allele frequencies for the genetic markers, indicating that the population structures are similar and the groups are appropriately matched. The adjustment comprises selectively removing "outlier" individuals from one or both groups. This process is depicted in FIG. 8, where an exemplary graph includes mean curves for case and control groups. The vertical axis represents the statistical mean population structure for the remaining individuals as derived from individual ethnicities calculated by the clustering algorithm. Stated another way, this mean represents the "average" population structure represented across the case or control group.

As shown, the horizontal axis represents the number of individuals in the group. Accordingly, as the number of individuals increases, the mean is recalculated for the new total number of individuals. Furthermore, the individuals are added along the horizontal axis in either ascending or descending order according to the individual's percentage of a particular ethnicity.

In the present example, the vertical axis represents the mean percentage of Native American ancestry (or whatever population structure component is appropriate for the study at hand) and the horizontal axis represents the number of individuals in a group. In this example, curve 802 represents the control group, curve 800 represents the case group. In the present example, cases tend to have a higher proportion of Native American ancestry than controls, so for matching we will generally want to select the cases with relatively low degrees of Native American ancestry, and the controls with relatively high degrees of Native American ancestry. Curve 800 shows the highest attainable mean degree of Native American ancestry that can be obtained for a given number of controls. Curve 802 shows the lowest attainable mean degree of Native American ancestry that can be obtained for a given number of cases. Balanced study designs should choose a number of cases, and a number of controls, for which the same degree of Native American ancestry can be obtained. Point 804, at the intersection of curves 800 and 802, represents one such balanced design, which would be optimal if equal numbers of cases and controls are desired.

The composition of the two groups need not always be chosen fall at the point of intersection. In fact, this might not be desirable. In some studies, it may be significantly easier to recruit controls than cases, and it may be better to choose a mean population structure for the case and control groups that yields a larger number of controls than cases. Graphically, this is represented by choosing sample sizes as the intersections of curves 800 and 802 with a horizontal line at the chosen mean population structure.

These graphs actually consist of discrete points corresponding to integer numbers of individuals and there will generally not be a point at which the means of the case and control groups are absolutely identical. Yet there will be a pair of points from the two curves where the mean values come closest. So one may chose these two closest points as the matching mean. Although a specific means matching technique is outlined here, it should be recognized that the case and control groups can be adjusted according to a variety of methods, depending on the application. If the analysis indicates that the case and control groups have substantial contributions from more than two ancestral populations, then a similar procedure of removing the most extreme individuals can still be employed.

A third matching method can be employed when the case and control groups are defined using ranges of a quantitative measurement. Rather than defining cases and controls, and then selecting subsets that are matched, the measurement can be adjusted to remove the effect of population structure anomalies, and then cases and controls can be selected based on the adjusted phenotype. One appropriate adjustment method involves using a multiple linear regression or general additive model to measure the influence of the estimated genetic population structure parameters on the measurement. For each experimental subject, the model is used to determine a fitted value representing the expected mean measurement for individuals with the same population structure. Subtracting these fitted values from the observed measurements, gives values that are "standardized" or corrected for the influence of population structure. Criteria for defining cases and controls can then be defined in terms of their adjusted measurements. This method can easily be applied regardless of the number of ancestral population clusters, as each cluster is simply represented by an additional independent variable in the regression analysis.

As should be apparent, embodiments of the present invention employ processes acting under control of instructions and/or data stored in or transferred through one or more computer systems. Embodiments of the present invention also relate to apparatus for performing these operations. Such apparatus may be specially designed and/or constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein. In some cases, however, it may be more convenient to construct a specialized apparatus to perform the required method operations. A particular structure for a variety of these machines will appear from the description given below.

In addition, embodiments of the present invention relate to computer readable media or computer program products that include program instructions and/or data (including data structures) for performing various computer-implemented operations. Examples of computer-readable media include, but are not limited to, magnetic media such as hard disks, floppy disks, magnetic tape; optical media such as CD-ROM devices and holographic devices; magneto-optical media; semiconductor memory devices, and hardware devices that are specially configured to store and perform program instructions, such as read-only memory devices (ROM) and random access memory (RAM), and sometimes application-specific integrated circuits (ASICs), programmable logic devices (PLDs) and signal transmission media for delivering computer-readable instructions, such as local area networks, wide area networks, and the Internet. The data and program instructions of this invention may also be embodied on a carrier wave or other transport medium (e.g., optical lines, electrical lines, and/or airwaves). Examples of program instructions include both machine code, such as produced by a compiler, and files containing higher level code that may be executed by the computer using an interpreter. Further, the program instructions include machine code, source code and any other code that directly or indirectly controls operation of a computing machine in accordance with this invention. The code may specify input, output, calculations, conditionals, branches, iterative loops, etc.

The various method operations described above may be implemented in whole or part on one or more computer systems. Often, it will be convenient to employ two or more computer systems to implement the invention. As an example, one system may serve to genotype the members of the case and control groups, while a different system determines the distribution of alleles within the groups and rebalances the groups if necessary. Such systems may share information via a computer network. In addition, separate computer program products (including their machine readable media) may be employed to house the program instructions for separate operations of the invention.

Figure 9A:
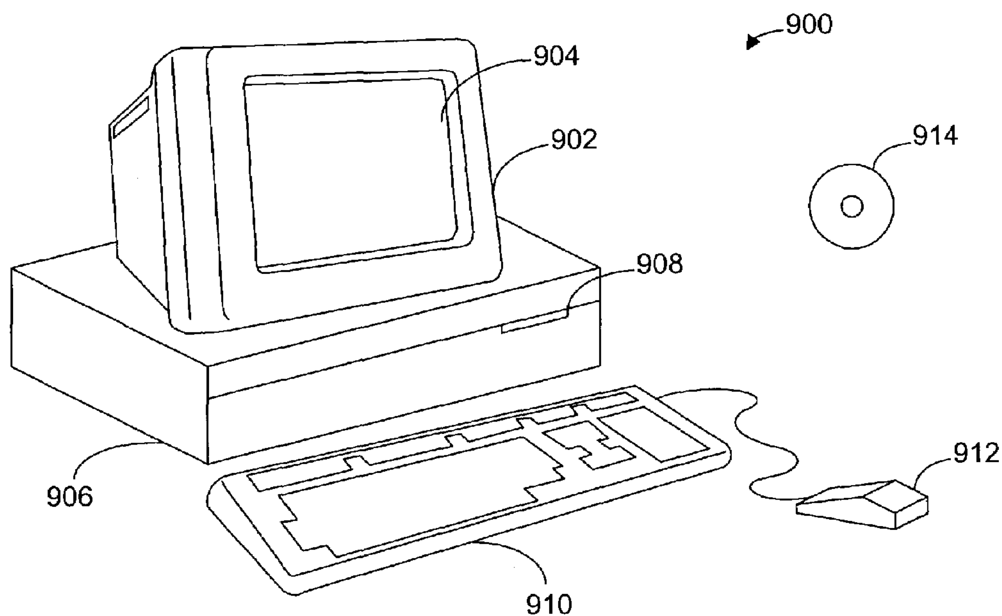
FIGS. 9A and 9B illustrate a computer system suitable for implementing embodiments of the present invention.
Figure 9B:
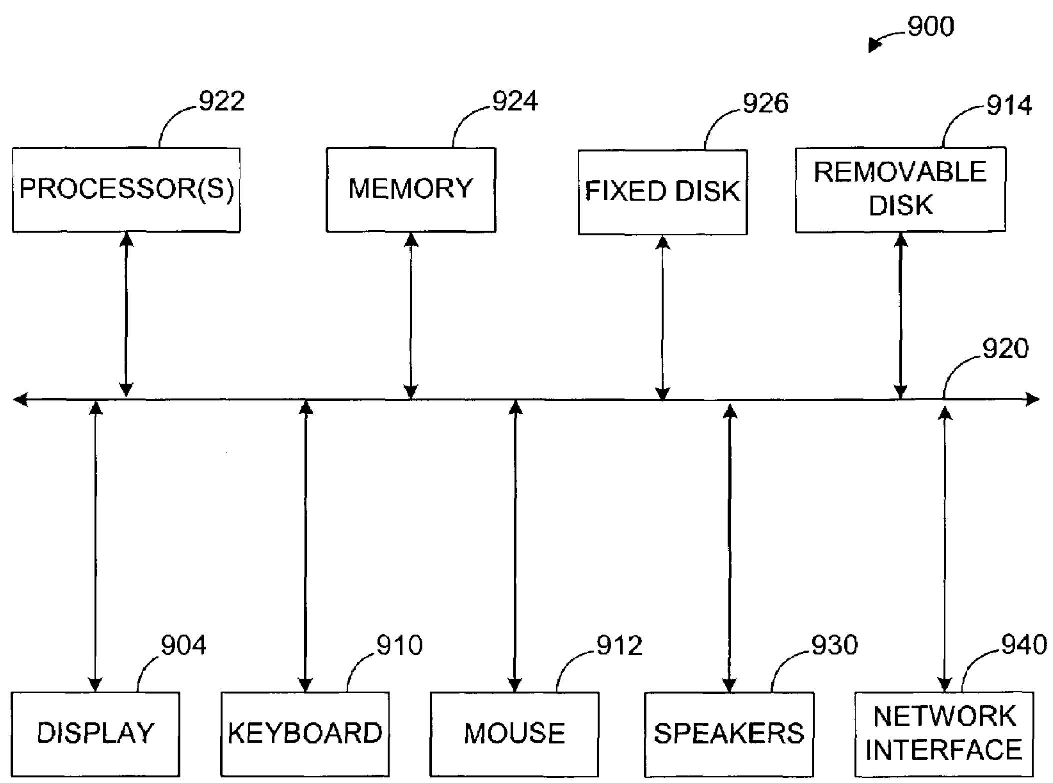

FIGS. 9A and 9B illustrate a computer system 900 suitable for implementing embodiments of the present invention. FIG. 9A shows one possible physical form of the computer system. Of course, the computer system may have many physical forms ranging from an integrated circuit, a printed circuit board and a small handheld device up to a very large super computer. Computer system 900 includes a monitor 902, a display 904, a housing 906, a disk drive 908, a keyboard 910 and a mouse 912. Disk 914 is one example of a computer-readable medium used to transfer data to and from computer system 900.

FIG. 9B is a block diagram of certain logical components of computer system 900. Attached to system bus 920 are a wide variety of subsystems. Processor(s) 922 (also referred to as central processing units, or CPUs) are coupled to storage devices including memory 924. Memory 924 includes random access memory (RAM) and read-only memory (ROM). ROM acts to transfer data and instructions uni-directionally to the CPU and RAM is used typically to transfer data and instructions in a bi-directional manner. Both of these types of memories may include any suitable computer-readable medium, including those described above. A fixed disk 926 is also coupled bi-directionally to CPU 922; it provides additional data storage capacity and may also include any of the computer-readable media described below. Fixed disk 926 may be used to store programs, data and the like and is typically a secondary storage medium (such as a hard disk) that is slower than primary storage. It will be appreciated that the information retained within fixed disk 926, may, in appropriate cases, be incorporated in standard fashion as virtual memory in memory 924. Removable disk 914 may take the form of any of the computer-readable media described below.

CPU 922 is also coupled to a variety of input/output devices such as display 904, keyboard 910, mouse 912 and speakers 930. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 922 optionally may be coupled to another computer or telecommunications network using network interface 940. With such a network interface, it is contemplated that the CPU might receive information from the network, or might output information to the network in the course of performing the above-described method steps. Furthermore, method embodiments of the present invention may execute solely upon CPU 922 or may execute over a network such as the Internet in conjunction with a remote CPU that shares a portion of the processing.

EXAMPLES

To test and compare the population structures of a case and a control population prior to performing an association study, 312 SNPs from a subset of individuals from each population were genotyped. Multiplex PCR was used to amplify genomic regions containing the 312 SNP loci, and a different primer pair was required for each SNP locus. The 312 primer pairs required to amplify the genomic regions containing the 312 SNP loci were pooled such that 13 primer pairs were included in each multiplex PCR. Thus, a total of 24 multiplex PCRs were required to amplify the 312 SNP loci for each individual to be tested.

The pooled primer pairs were diluted to a final concentration of 2.5 μM with TE resulting in 10.34 ml of a pooled primer stock solution. Then, for one pooled primer stock solution, 114 μl was aliquoted into each of the wells in a predetermined region on a multi-well plate ("Primer Stock Plate"). This was repeated for each of the pooled primer stock solutions such that aliquots of each occupied different regions on the Primer Stock Plates. Thus, a total of 24 regions were required to hold the aliquots from the 24 pooled primer stock solutions, and these regions were contained on a total of six multi-well plates (four regions per plate). The Primer Stock Plates were stored at −20° C. until required for preparation of PCR Plates, as described infra.

Prior to use, 2 μl from each well of a Primer Stock Plate was transferred into a well in a corresponding location on a second multi-well plate ("PCR Plate"). This was repeated for the same Primer Stock Plate for 49 additional PCR Plates. The transfer from a single Primer Stock Plate to 50 PCR Plates was repeated for the other five Primer Stock Plates. The resulting PCR Plates were stored at −20° C. until required for carrying out PCR, as described infra.

Each DNA sample to be genotyped was diluted with water to a final concentration of 2.5 ng/μl. Buffer for PCR was prepared as follows.

For each PCR reaction:

| PCR buffer components | Volume |
|---|---|
| Water | 2.25 μl |
| 10X AK2 | 1.47 μl |
| 1M Tricine | 0.38 μl |
| 10X Enhancer | 0.67 μl |
| 100% DMSO | 0.47 μl |
| Total PCR buffer | 5.24 μl |

After preparing the PCR buffer, dNTPs and Titanium Taq polymerase (Clontech (BD Biosciences), Palo Alto, Calif.) were added, in that order, to create the "PCR cocktail" as follows:

For each PCR reaction:

| To be added to PCR buffer | Volume |
|---|---|
| 25 mM of each dNTP | 0.26 μl |
| 50X Titanium Taq (Clontech) | 0.5 μl |
| Total PCR cocktail | 6.0 μl |

The volume for the PCR buffer was scaled up depending on how many PCR reactions were to be performed. Likewise, the amounts of dNTPs and Taq polymerase were also scaled up.

Then, for each individual DNA sample, 100 μm of the diluted DNA was added to 150 μl of PCR cocktail to create a Master Mix, 10 μl of which was then added to a set of wells on PCR plates, each of which contained 2 ul of one of the 13 pooled primer stock solutions. In this way, 24 multiplex PCRs were prepared for each individual DNA sample. Once each individual DNA sample was combined with PCR cocktail and each of the pooled primer stock solutions, PCRs could be performed on a thermocycler. The PCR cycle conditions were as follows:

| Temperature | Time | Number of cycles |
|---|---|---|
| 96° C. | 5 min | 1 |
| 96° C. | 30 seconds | 10 |
| 58° C. (−0.5° C. per cycle) | 30 seconds | |
| 65° C. | 60 seconds | |
| 96° C. | 10 seconds | 40 |
| 53° C. | 30 seconds | |
| 65° C. | 60 seconds | |
| 65° C. | 7 minutes | 1 |
| 4° C. | indefinitely | |

After the PCR was complete, the plates were centrifuged briefly at 1500 rpm and stored at −20° C. until required for pooling, as described infra.

Next, the products of the 312 PCRs for the 312 SNPs were pooled together for each individual from which a DNA sample was amplified. The PCR product pools were then diluted 1:25 with water. These diluted, pooled PCR products were stored at −20° C. until required for quantification, as described infra.

The quantification of the diluted, pooled PCR products was performed using PicoGreen dsDNA Quantitation Reagent (Molecular Probes, Inc., Eugene, Oreg.) in combination with a Cytofluor system (Applied Biosystems, Foster City, Calif.) or Spectraphor Plus (Tecan Instruments, Maennedorf, Switzerland) according to manufacturer's instructions. A DNA concentration of less than 10 ng/μl was indicative that the PCR had failed and the sample was not processed further. An acceptable DNA concentration was between 15 and 30 ng/μl. If the concentration was higher, then the DNA was diluted to adjust the average concentration to 25 ng/μl.

After quantification of the pooled PCR products, 10 μl of each was labeled with biotin (biotin stock solution=1 mM of a 1:1 mix of b-ddUTP and b-dUTP) using the following labeling mix:

Per 10 μl DNA sample

| Labeling Mix Component | Volume |
|---|---|
| 10X One-Phor-All Buffer | 3.6 μl |
| Biotin stock solution | 0.0156 μl |
| Water | 22.32 μl |
| Recombinant TdT (400 U/μl) | 0.0625 μl |
| Total Labelin Mix | 26 μl |

The volume for the Labeling Mix was scaled up depending on how many DNA samples were to be labeled. The One-Phor-All buffer, the biotin-labeled nucleotides, and the recombinant TdT were from Amersham Biosciences (Piscataway, N.J.), Enzo (Farmingdale, N.Y.), and Roche Diagnostics (Basel, Switzerland), respectively. The labeling reaction was performed on a thermocycler under the following conditions:

| Temperature | Time |
|---|---|
| 37° C. | 90 minutes |
| 99° C. | 10 minutes |
| 4° C. | indefinitely |

The samples were then stored at −20° C. until it was time to hybridize them to stratification chips. The hybridization buffer used was as follows:

| Hybridization buffer components | Per chip | Per plate |
|---|---|---|
| 5M TMACL | 60 μl | 5640 μl |
| 1% Triton X-100 | 1 μl | 94 μl |
| 5 nM b-948 oligo | 1 μl | 94 μl |
| 10 μg/μl herring sperm DNA | 1 μl | 94 μl |
| 1 M Tris, pH 7.8 | 1 μl | 94 μl |
| Total hybridization buffer | 64 μl | 6016 μl |

64 μl of hybridization buffer was added to each labeled sample prior to denaturation at 99° C. for 10 minutes, after which the denatured samples were cooled to 50° C. Each oligonucleotide array chip (hereafter "chip") was prewarmed in a 50° C. incubator. Then, 100 μl of a denatured sample was transferred to a chip. This process was repeated for all denatured samples. Chips containing denatured samples were transferred to a 50° C. hybridization oven and rotated at 25 rpm for at least 12 hours.

The hybridized chips were then stained, washed, and scanned on a laser scanner. The data from the scans was processed to reveal the genotypes of the 312 SNPs for the subsets of individuals from the case and control groups, and these genotypes were used to determine whether the population structures of the two groups was matched, as described in the Detailed Description supra.

Conclusion

Although the above generally describes the present invention according to specific exemplary processes, various modifications can be made without departing from the spirit and/or scope of the present invention. Therefore, the present invention should not be construed as being limited to the specific forms shown in the appended figures and described above.

What is claimed is:

1. A method for identifying matched groups prior to performing a study, the method comprising:

prior to performing a study, identifying members of a control group and members of a case group;

for each of a number of selected genetic markers, genotyping a plurality of members in the control group and a plurality of members in the case group, wherein the genotyping identifies a set of alleles corresponding to the genetic markers for each member of the pluralities, and wherein the genetic markers are selected to identify differences in population structure between members; and determining if the groups are matched based on the genotypes of said case group and said control group by (i) determining observed chi-squared score statistics of association with a phenotype based on counts of each genetic marker allele among members of the case and control groups;

(ii) comparing a distribution of the observed chi-squared score statistics with an expected chi-squared score statistics distribution in a Q—Q plot; and (iii) determining if the differences between the observed and expected statistics distributions exceed an acceptable range, wherein if the differences between the observed and expected statistics distributions do not exceed an acceptable range the groups are determined to be matched.

2. A method for identifying matched groups prior to performing a study, the method comprising:

prior to performing a study, identifying members of a control group and members of a case group;

for each of a number of selected genetic markers, genotyping a plurality of members in the control group and a plurality of members in the case group, wherein the genotyping identifies a set of alleles corresponding to the genetic markers for each member of the pluralities, and wherein the genetic markers are selected to identify differences in population structure between members; and determining if the groups are matched based on the genotypes of said case group and said control group by (i) determining observed chi-squared score statistics of association with a phenotype based on counts of each genetic marker allele among members of the case and control groups;

(ii) for each genetic marker, determining a p-value based on the observed chi-squared score statistics;

(iii) comparing the distribution of smaller p-values for the observed chi-squared score statistics with an expected distribution of small p-values for chi-squared score statistics; and (iv) determining if the differences between the observed and expected distributions exceed an acceptable range, wherein if the differences between the observed and expected statistics do not exceed an acceptable range the groups are determined to be matchet.

3. A method for identifying watched groups prior to performing a study, the method comprising:

prior to performing a study, identifying members of a control group and members of a case group;

for each of a number of selected genetic markers, genotyping a plurality of members in the control group and a plurality of members in the case group, wherein the genotyping identifies a set of alleles corresponding to the genetic markers for each member of the pluralities, and wherein the genetic markers are selected to identify differences in population structure between members; and determining if the groups are matched based on the genotypes of said case group and said control group by (i) determining observed chi-squared score statistics of association with a phenotype based on counts of each genetic marker allele among members of the case and control groups;

(ii) computing a global p-value based on the sum of individual observed chi-squared score statistics; and (iii) determining if the global p-value for the given number of individuals in the study exceeds an acceptable threshold, wherein if the global p-value does exceed an acceptable threshold the groups are determined to be matched.

4. A method for identifying matched groups prior to performing a study, the method comprising:

prior to performing a study, identifying members of a control group and members of a case group;

for each of a number of selected genetic markers, genotyping a plurality of members in the control group and a plurality of members in the case group, wherein the genotyping identifies a set of alleles corresponding to the genetic markers for each member of the pluralities, and wherein the genetic markers are selected to identify differences in population structure between members; and determining if the groups are matched based on the genotypes of said case group and said control group by (i) determining observed chi-squared score statistics of association with a phenotype based on counts of each genetic marker allele among members of the case and control groups;

(ii) comparing a distribution of the observed chi-squared score statistics with an expected chi-squared score statistics distribution in a Q—Q plot; and (iii) determining if the differences between the observed and expected statistics distributions exceed an acceptable range, wherein if the differences between the observed and expected statistics distributions do not exceed an acceptable range the groups are determined to be matched, wherein the genetic markers are highly polymorphic across a set of globally diverse individuals, and wherein said globally diverse individuals comprise individuals with African, Asian, European, Native South American, and Native North American ancestry.

5. A method for identifying matched groups prior to performing a study, the method comprising:

prior to performing a study, identifying members of a control group and members of a case group;

for each of a number of selected genetic markers, genotyping a plurality of members in the control group and a plurality of members in the case group, wherein the genotyping identifies a set of alleles corresponding to the genetic markers for each member of the pluralities, and wherein the genetic markers are selected to identify differences in population structure between members; and determining if the groups are matched based on the genotypes of said case group and said control group by (i) determining observed chi-squared score statistics of association with a phenotype based on counts of each genetic marker allele among members of the case and control groups;

(ii) comparing a distribution of the observed chi-squared score statistics with an expected chi-squared score statistics distribution in a Q—Q plot; and (iii) determining if the differences between the observed and expected statistics distributions exceed an acceptable range, wherein if the differences between the observed and expected statistics distributions do not exceed an acceptable range the groups are determined to be matched, wherein the genetic markers are 312 single nucleotide polymorphisms described in Table 1.

6. The method of claim 1, further comprising using the control group and the case group in an association study if the difference between the observed chi-squared test statistic distribution and expected chi-squared distribution does not exceed an acceptable range.

7. The method of claim 1, further comprising adjusting the members of either or both of the control group and case group if the difference between the observed chi-squared test statistic distribution and expected chi-squared distribution does exceed an acceptable range.

8. The method of claim 7, such that the adjusting results in the chi-squared test statistic distribution being similar to the expected chi-squared distribution.

9. The method of claim 7, where the adjustment is based on results of a clustering analysis of the genotype data, and wherein the clustering analysis is used to estimate the proportional contribution of two or more ancestral human populations to the genetic background of each member of the pluralities.

10. The method of claim 7, where adjusting includes assigning individuals in the case and control groups to strata based on their estimated ancestry, and then removing a minimum number of individuals such that the proportion of cases in each of the strata is nearly the same.

11. The method of claim 7, wherein the adjusting includes:

removing members of either or both of the case and control groups until the average population structure for the case and control groups is equivalent.

12. The method of claim 7, wherein adjusting includes (i) performing a regression analysis of the quantitative phenotype of interest against the population structure estimates, and then (ii) defining adjusted case and control groups based on adjusted measurements where the expected contribution of an individual's ancestry, determined from the regression analysis, is subtracted from that individual's phenotype measurement.

13. A method for identifying matched groups prior to performing a study, the method comprising:

prior to performing a study, identifying members of a control group and members of a case group;

for each of a number of selected genetic markers, genotyping a plurality of members in the control group and a plurality of members in the case group, wherein the genotyping identifies a set of alleles corresponding to the genetic markers for each member of the pluralities, and wherein the genetic markers are selected to identify differences in population structure between members; and determining if the groups are matched based on the genotypes of said case group and said control group by (i) determining observed chi-squared score statistics of association with a phenotype based on counts of each genetic marker allele among members of the case and control groups;

(ii) comparing a distribution of the observed chi-squared score statistics with an expected a chi-squared score statistics distribution in a Q—Q plot; and (iii) determining if the differences between the observed and expected statistics distributions exceed an acceptable range, wherein if the differences between the observed and expected statistics distributions do not exceed an acceptable range the groups are determined to be matched, wherein the selected genetic markers are (i) polymorphic across globally diverse individuals, separated along a genome by at least about 5 megabases, and (ii) separated from repeat sequences by at least about 150 base pairs.

14. A method for performing an association study comprising:

prior to performing the study, identifying members of a control group and members of a case group;

for each of a number of selected genetic markers, genotyping a plurality of members in the control group and a plurality of members in the case group, wherein the genotyping identifies a set of alleles corresponding to the genetic markers for each member of the pluralities, and wherein the genetic markers are selected to identify differences in population structure between members;

determining if the groups are matched based on the genotypes of said case group and said control group by (i) determining observed chi-squared score statistics of association with a phenotype based on counts of each genetic marker allele among members of the case and control groups;

(ii) comparing a distribution of the observed chi-squared score statistics with an expected chi-squared score statistics distribution in a Q—Q plot; and (iii) determining if the differences between the observed and expected statistics distributions exceed an acceptable range, wherein if the differences between the observed and expected statistics distributions do not exceed an acceptable range the groups are determined to be matched;

adjusting the case and control groups if these nouns are not matched such that they become matched; and then comparing the case and control groups to identify genetic loci that correlate wit a phenotypic trait of interest, wherein adjusting the case and control groups comprises:

(i) performing a stratification analysis on the case and control groups; and (ii) balancing the relative contributions of strata identified by the stratification analysis across the case and control groups by gradually removing outlier individuals from one or more of these groups and recomputing mean allele frequencies for the one or both of the case and control groups until the mean allele frequencies reach an acceptable level similarity.

15. A method for detecting and correcting population structure of study groups so that they are matched, said method comprising;

a) identifying members of a control group and members of a case group;

b) for each of a number of selected genetic markers, genotyping a plurality of members in the control group and a plurality of members in the case group, wherein the genotyping identifies a set of alleles corresponding to the genetic markers for each member of the pluralities, wherein the genetic markers are selected to identify differences in population structure between members, and wherein the genetic markers include one or more of the single nucleotide polymorphisms described in Table 1; and c) determining if the groups are matched based on the genotypes of said case group and said control group by (i) determining observed chi-squared score statistics of association with a phenotype based on counts of each genetic marker allele among members of the case and control groups;

(ii) comparing a distribution of the observed chi-squared score statistics with an expected chi-squared score statistics distribution in a Q—Q plot; and (iii) determining if the differences between the observed and expected statistics distributions exceed an acceptable range, wherein if the differences between the observed and expected statistics distributions do not exceed an acceptable range the groups are determined to be matched.

16. A computer program product comprising a machine readable medium on which is provided program instructions for matching population structure of case and control groups prior to performing a study, the program instructions comprising:

code for determining if the case and control groups are matched based on genotypes of said case group and said control group, wherein said genotypes were obtained by genotyping a plurality of members in the control group and a plurality of members in the case group, wherein the genotyping identifies a set of alleles corresponding to each of a number of selected genetic markets for each member of the pluralities and wherein the genetic markers are selected to identify differences in population structure between members, wherein the code for determining of the case and control groups are matched comprises (i) code for determining observed chi-squared score statistics of association with a phenotype based on counts of each genetic marker allele among members of the case and control groups;

(ii) code for comparing a distribution of the observed chi-squared score statistics with an expected chi-squared score statistics distribution in a Q—Q plot; and (iii) code for determining if the differences between the observed and expected statistics distributions exceed an acceptable range, wherein if the differences between the observed and expected statistics distributions do not exceed an acceptable range the groups are determined to be matched; and code for adjusting the study populations that are not matched such that they become matched by (i) performing a stratification analysis on the case and control groups; and (ii) balancing the relative contributions of strata identified by the stratification analysis across the case and control groups by gradually removing outlier individuals from one or more of these groups and recomputing mean allele frequencies for the one or more groups until the mean allele frequencies reach an acceptable level similarity.

17. A method for identifying matched groups prior to performing a study, the method comprising:

prior to performing a study, identifying members of a control group and members of a case group;

for each of a number of selected genetic markers, genotyping a plurality of members in the control group and a plurality of members in the case group, wherein the genotyping identifies a set of alleles corresponding to the genetic markers for each member of the pluralities, and wherein the genetic markers are selected to identify differences in population structure between members; and determining if the groups are matched based on the genotypes of said case group and said control group by (i) determining observed chi-squared score statistics of association with a phenotype based on counts of each genetic marker allele among members of the case and control groups;

(ii) for each genetic marker, determining a p-value based on the observed chi-squared score statistics;

(iii) comparing the distribution of smaller p-values for the observed chi-squared score statistics with an expected distribution of small p-values for chi-squared score statistics; and (iv) determining if the differences between the observed and expected distributions exceed an acceptable range, wherein if the differences between the observed and expected statistics do not exceed an acceptable range the groups are determined to be matched, wherein the genetic markers are highly polymorphic across a set of globally diverse individuals, and wherein said globally diverse individuals comprise individuals with African, Asian, European, Native South American, and Native North American ancestry.

18. A method for identifying matched groups prior to performing a study, the method comprising:

prior to performing a study, identifying members of a control group and members of a case group;

for each of a number of selected genetic markers, genotyping a plurality of members in the control group and a plurality of members in the case group, wherein the genotyping identities a set of alleles corresponding to the genetic markers far each member of the pluralities, and wherein the genetic markers are selected to identify differences in population structure between members; and determining if the groups are matched based on the genotypes of said case group and said control group by (i) determining observed chi-squared score statistics of association with a phenotype based on counts of each genetic marker allele among members of the case and control groups;

(ii) for each genetic marker, determining a p-value based on the observed chi-squared score statistics;

(iii) comparing the distribution of smaller p-values for the observed chi-squared score statistics with an expected distribution of small p-values for chi-squared score statistics; and (iv) determining if the differences between the observed and expected distributions exceed an acceptable range, wherein if the differences between the observed and expected statistics do not exceed an acceptable range the groups are determined to be matched, wherein the genetic markers are 312 single nucleotide polymorphisms described in Table 1.

19. A method for identifying matched groups prior to performing a study, the method comprising:

prior to performing a study, identifying members of a control group and members of a case group;

for each of a number of selected genetic markers, genotyping a plurality of members in the control group and a plurality of members in the case group, wherein the genotyping identifies a set of alleles corresponding to the genetic markers for each member of the pluralities, and wherein the genetic markers are selected to identify differences in population structure between members; and determining if the groups are matched based on the genotypes of said case group and said control group by (i) determining observed chi-squared score statistics of association with a phenotype based on counts of each genetic marker allele among members of the case and control groups;

(ii) for each genetic marker, determining a p-value based on the observed chi-squared score statistics;

(iii) comparing the distribution of smaller p-values for the observed chi-squared score statistics with an expected distribution of small p-values for chi-squared score statistics; and (iv) determining if the differences between the observed and expected distributions exceed an acceptable range, wherein if the differences between the observed and expected statistics do not exceed an acceptable range the groups are determined to be matched, wherein the selected generic markers are (i) polymorphic across globally diverse individuals, separated along a genome by at least about 5 megabases, and (ii) separated from repeat sequences by at least about 150 base pairs.

20. A method for performing an association study comprising:

prior to performing the study, identifying members of a control group and members of a case group;

for each of a number of selected genetic markers, genotyping a plurality of members in the control group and a plurality of members in the case group, wherein the genotyping identifies a set of alleles corresponding to the genetic markers for each member of the pluralities, and wherein the genetic markers are selected to identify differences in population structure between members;

determining if the groups are matched based on the genotypes of said case group and said control group by (i) determining observed chi-squared score statistics of association with a phenotype based on counts of each genetic marker allele among members of the case and control groups;

(ii) for each genetic marker, determining a p-value based on the observed chi-squared score statistics;

(iii) comparing the distribution of smaller p-values for the observed chi-squared score statistics with an expected distribution of small p-values for chi-squared score statistics; and (iv) determining if the differences between the observed and expected distributions exceed an acceptable range, wherein if the differences between the observed and expected statistics do not exceed an acceptable range to groups are determined to be matched;

adjusting the case and control groups if these groups are not matched such that they become matched, and then comparing the case and control groups to identify genetic loci that correlate with a phenotypic trait of interest, wherein adjusting the case and control groups comprises:

(i) performing a stratification analysis on the case and control groups; and (ii) balancing the relative contributions of strata identified by the stratification analysis across the case and control groups by gradually removing outlier individuals from one or more of these groups and recomputing mean allele frequencies for the one or both of the case and control groups until the mean allele frequencies reach an acceptable level similarity.

21. A method for detecting and correcting population structure of study groups so that they are matched, said method comprising;

a) identifying members of a control group and members of a case group;

b) for each of a number of selected genetic markers, genotyping a plurality of members in the control group and a plurality of members in the case group, wherein the genotyping identifies a set of alleles corresponding to the genetic markers for each member of the pluralities, wherein the genetic markers are selected to identify differences in population structure between members, and wherein the genetic markers include one or more of the single nucleotide polymorphisms described in Table 1; and c) determining if the groups are matched based on the genotypes of said case group and said control group by (i) determining observed chi-squared score statistics of association with a phenotype based on counts of each genetic marker allele among members of the case and control groups;

(ii) for each genetic marker, determining a p-value based on the observed chi-squared score statistics;

(iii) comparing the distribution of smaller p-values for the observed chi-squared score statistics with an expected distribution of small p-values for chi-squared score statistics; and (iv) determining if the differences between the observed and expected distributions exceed an acceptable range, wherein if the differences between the observed and expected statistics do not exceed an acceptable range the groups are determined to be matched.

22. A computer program product comprising a machine readable medium on which is provided program instructions for matching population structure of case and control groups prior to performing a study, the program instructions comprising:

code for determining if the case and control groups are matched based on genotypes of said case group and said control group, wherein said genotypes were obtained by genotyping a plurality of members in the control group and a plurality of members in the case group, wherein the genotyping identifies a set of alleles corresponding to each of a number of selected genetic markers for each member of the pluralities, and wherein the genetic markers are selected to identify differences in population structure between members, wherein the code for determining if the case and control groups are matched comprises (i) code for determining observed chi-squared score statistics of association with a phenotype based on counts of each genetic marker allele among members of the case and control groups;

(ii) code for determining, for each genetic marker, a p-value based on the observed chi-squared score statistics;

(iii) code for comparing the distribution of smaller p-values for the observed chi-squared score statistics with an expected distribution of small p-values for chi-squared score statistics; and (iv) code for determining if the differences between the observed and expected distributions exceed an acceptable range, wherein if the differences between the observed and expected statistics do not exceed an acceptable range the groups are determined to be matched; and code for adjusting the study populations that are not matched such that they become matched by (i) performing a stratification analysis on the case and control groups; and (ii) balancing the relative contribution of strata identified by the stratification analysis across the case and control groups by gradually removing outlier individuals from one or more of these groups and recomputing mean allele frequencies for the one or more groups until the mean allele frequencies reach an acceptable level similarity.

23. A method for identifying matched groups prior to performing a study, the method comprising:

prior to performing a study, identifying members of a control group and members of a case group;

for each of a number of selected genetic markers, genotyping a plurality of members in the control group and a plurality of members in the case group, wherein the genotyping identifies a set of alleles corresponding to the genetic markers for each member of the pluralities, and wherein the genetic markers are selected to identify differences in population structure between members; and determining if the groups are matched based on the genotypes of said case group and said control group by (i) determining observed chi-squared score statistics of association with a phenotype based on counts of each genetic marker allele among members of the case and control groups;

(ii) computing a global p-value based on the sum of individual observed chi-squared score statistics; and (iii) determining if the global p-value for the given number of individuals in the study exceeds an acceptable threshold, wherein if the global p-value does exceed an acceptable threshold the groups are determined to be watched, wherein the genetic markers are highly polymorphic across a set of globally diverse individuals, and wherein said globally diverse individuals comprise individuals with African, Asian, European, Native South American, and Native North American ancestry.

24. A method for identifying matched groups prior to performing a study, the method comprising:

prior to performing a study, identifying members of a control group and members of a case group;

for each of a number of selected genetic markers, genotyping a plurality of members in the control group and a plurality of members in the case group, wherein the genotyping identifies a set of alleles corresponding to the genetic markers for each member of the pluralities, and wherein the genetic markers are selected to identify differences in population structure between members; and determining if the groups are matched based on the genotypes of said case group and said control group by (i) determining observed chi-squared score statistics of association with a phenotype based on counts of each genetic marker allele among members of the case and control groups;

(ii) computing a global p-value based on the sum of individual observed chi-squared score statistics; and (iii) determining if the global p-value for the given number of individuals in the study exceeds an acceptable threshold, wherein if the global p-value does exceed an acceptable threshold the groups are determined to be matched, wherein the genetic markers are 312 single nucleotide polymorphisms described in Table 1.

25. A method for identifying watched groups prior to performing a study, the method comprising:

prior to performing a study, identifying members of a control group and members of a case group;

for each of a number of selected genetic markers, genotyping a plurality of members in the control group and a plurality of members in the case group, wherein the genotyping identifies a set of alleles corresponding to the genetic markers for each member of the pluralities, and wherein the genetic markers are selected to identify differences in population structure between members; and determining if the groups are matched based on the genotypes of said case group and said control group by (i) determining observed chi-squared score statistics of association with a phenotype based on counts of each genetic marker allele among members of the case and control groups;

(ii) computing a global p-value based on the stun of individual observed chi-squared score statistics; and (iii) determining if the global p-value for the given number of individuals in the study exceeds an acceptable threshold, wherein if the global p-value does exceed an acceptable threshold the groups are determined to be matched, wherein the selected genetic markers (i) polymorphic across globally diverse individuals, separated along a genome by at least about 5 megabases, and (ii) separated from repeat sequences by at least about 150 base pairs.

26. A method for performing an association study comprising:

prior to performing the study, identifying members of a control group and members of a case group;

for each of a number of selected genetic markers, genotyping a plurality of members in the control group and a plurality of members in the case group, wherein the genotyping identifies a set of alleles corresponding to the genetic markers for each member of the pluralities, and wherein the genetic markers are selected to identify differences in population structure between members;

determining if the groups are matched based on to genotypes of said case group and said control group by (i) determining observed chi-squared score statistics of association with a phenotype based on counts of each genetic marker allele among members of the case and control groups;

(ii) computing a global p-value based on the sum of individual observed chi-squared score statistics; and (iii) determining if the global p-value for the given number of individuals in the study exceeds an acceptable threshold, wherein if the global p-value does exceed an acceptable threshold the groups are determined to be matched;

adjusting the case and control groups if these groups are not matched such that they become matched; and then comparing the case and control groups to identify genetic loci that correlate with a phenotypic trait of interest, wherein adjusting the case and control groups comprises:

(i) performing a stratification analysis on the case and control groups; and (ii) balancing the relative contributions of strata identified by the stratification analysis across the case and control groups by gradually removing outlier individuals front one or more of these groups and recomputing mean allele frequencies for the one or both of the case and control groups until the mean allele frequencies reach an acceptable level similarity.

27. A method for detecting and correcting population structure of study groups so that they are matched, said method comprising;

a) identifying members of a control group and members of a case group;

b) for each of a number of selected genetic markers, genotyping a plurality of members in the control group and a plurality of members in the case group, wherein the genotyping identifies a set of alleles corresponding to the genetic markers for each member of the pluralities, wherein the genetic markers are selected to identify differences in population structure between members, and wherein the genetic markers include one or more of the single nucleotide polymorphisms described in Table 1; and c) determining if the groups are matched based on the genotypes of said case group and said control group by (i) determining observed chi-squared score statistics of association with a phenotype based on counts of each genetic marker allele among members of the case and control groups;

(ii) computing a global p-value based on the sum of individual observed chi-squared score statistics; and (iii) determining if the global p-value for the given number of individuals in the study exceeds an acceptable threshold, wherein if the global p-value does exceed an acceptable threshold the groups are determined to be matched.

28. A computer program product comprising a machine readable medium on which is provided program instructions for matching population structure of ease and control groups prior to performing a study, the program instructions comprising:

code for determining if the case and control groups are matched based on genotypes of said case group and said control group, wherein said genotypes were obtained by genotyping a plurality of members in the control group and a plurality of members in the case group, wherein the genotyping identifies a set of alleles corresponding to each of a number of selected genetic markers for each member of the pluralities, and wherein the genetic markers are selected to identify differences in population structure between members, wherein the code for determining if the case and control groups are matched comprises (i) code for determining observed chi-squared score statistics of association with a phenotype based on counts of each genetic maker allele among members of the case and control groups;

(ii) code for computing a global p-value based on the sum of individual observed chi-squared score statistics; and (iii) code for determining if the global p-value for the given number of individuals in the study exceeds an acceptable threshold, wherein if the global p-value does exceed an acceptable threshold the groups are determined to be matched; and code for adjusting the study populations that are not matched such that they become matched by (i) performing a stratification analysis on the case and control groups; and (ii) balancing the relative contributions of strata identified by the stratification analysis across the case and control groups by gradually removing outlier individuals from one or more of these groups and recomputing mean allele frequencies for the one or more groups until the mean allele frequencies reach an acceptable level similarity.

* * * * *